US011471204B2

United States Patent
Vogt et al.

(10) Patent No.: US 11,471,204 B2
(45) Date of Patent: Oct. 18, 2022

(54) DEVICE FOR MIXING A BONE CEMENT WITH HOLLOW SPACE FOR MONOMER TRANSFER

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 257 days.

(21) Appl. No.: 16/705,969

(22) Filed: Dec. 6, 2019

(65) Prior Publication Data
US 2020/0179024 A1 Jun. 11, 2020

(30) Foreign Application Priority Data
Dec. 7, 2018 (DE) .................... 10 2018 131 268.7

(51) Int. Cl.
*A61B 17/88* (2006.01)
*B01F 23/53* (2022.01)
(Continued)

(52) U.S. Cl.
CPC .......... *A61B 17/8833* (2013.01); *B01F 23/53* (2022.01); *B01F 35/7131* (2022.01);
(Continued)

(58) Field of Classification Search
CPC ...... A61B 2017/8838; A61C 5/62; A61C 5/64
See application file for complete search history.

(56) References Cited

U.S. PATENT DOCUMENTS

| 2,446,501 A | 12/1944 | Weber |
| 2,591,046 A | 4/1952 | Brown |

(Continued)

FOREIGN PATENT DOCUMENTS

| CN | 108421132 | 8/2018 |
| DE | 3640279 | 6/1987 |

(Continued)

OTHER PUBLICATIONS

Non-Final Office Action dated Mar. 24, 2022 in U.S. Appl. No. 16/655,345.

(Continued)

*Primary Examiner* — Nicholas W Woodall
(74) *Attorney, Agent, or Firm* — Dicke, Billig & Czaja, PLLC

(57) ABSTRACT

One embodiment relates to a device for the production of a bone cement dough from a monomer liquid and a cement powder comprising a cartridge with an internal space; a cartridge head with a dispensing opening; a conveying plunger that is arranged in the internal space of the cartridge and is supported in the internal space of the cartridge such that it is pushable in the direction of the dispensing opening; a dispensing plunger between the dispensing opening and the conveying plunger that is supported in the internal space of the cartridge such that it is pushable in the direction of the dispensing opening; a first hollow space, in which the cement powder is arranged; a second hollow space that is bordered by the dispensing plunger and the conveying plunger; a fluid opening that is arranged in the conveying plunger; a feedthrough that connects the first hollow space and the second hollow space to each other, and a closure means that is arranged on a rear side of the dispensing plunger. The closure means projects away from the dispensing plunger and is situated at a distance from the fluid (Continued)

opening. The fluid opening is closable with the closure means. The closure means is mobile in the closed fluid opening such that the fluid opening stays closed, while the conveying plunger is pushable further in the direction of the dispensing plunger.

17 Claims, 11 Drawing Sheets

(51) Int. Cl.
  *B01F 35/71*        (2022.01)
  *B01F 35/75*        (2022.01)
  *A61B 17/00*        (2006.01)
  *B01F 23/50*        (2022.01)
  *B01F 101/20*       (2022.01)
(52) U.S. Cl.
  CPC .. *B01F 35/7174* (2022.01); *B01F 35/754251* (2022.01); *A61B 17/8825* (2013.01); *A61B 2017/00526* (2013.01); *A61B 2017/8838* (2013.01); *B01F 23/565* (2022.01); *B01F 2101/20* (2022.01)

(56) References Cited

U.S. PATENT DOCUMENTS

| | | | |
|---|---|---|---|
| 2,754,590 A * | 7/1956 | Cohen | A61C 5/50 433/90 |
| 2,869,543 A | 1/1959 | Ratcliff et al. | |
| 3,028,052 A * | 4/1962 | Archer | B01F 35/7137 222/386 |
| 3,164,303 A | 1/1965 | Trautmann | |
| 3,464,412 A | 9/1969 | Schwartz | |
| 3,480,014 A * | 11/1969 | Callahan | A61M 5/24 604/506 |
| 3,659,749 A | 5/1972 | Schwartz | |
| 3,684,136 A * | 8/1972 | Baumann | A61M 3/005 604/416 |
| 3,739,947 A * | 6/1973 | Baumann | B05C 17/00593 604/416 |
| 3,785,379 A | 1/1974 | Cohen | |
| 4,391,590 A | 7/1983 | Dougherty | |
| 4,648,532 A | 3/1987 | Green | |
| 4,671,263 A | 6/1987 | Draenert | |
| 4,758,096 A | 7/1988 | Gunnarsson | |
| 4,898,580 A | 2/1990 | Crowley | |
| 4,968,299 A | 11/1990 | Ahlstrand et al. | |
| 4,972,969 A | 11/1990 | Randklev | |
| 4,973,168 A | 11/1990 | Chan | |
| 5,026,283 A * | 6/1991 | Osanai | A61C 5/66 604/87 |
| 5,100,241 A | 3/1992 | Chan | |
| 5,344,232 A | 9/1994 | Nelson et al. | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,779,356 A | 7/1998 | Chan | |
| 5,971,953 A | 10/1999 | Bachynsky | |
| 5,997,544 A | 12/1999 | Nies et al. | |
| 6,017,349 A | 1/2000 | Heller et al. | |
| 6,033,105 A | 3/2000 | Barker et al. | |
| 6,120,174 A | 9/2000 | Hoag et al. | |
| 6,386,872 B1 * | 5/2002 | Mukasa | A61C 5/64 222/570 |
| 6,544,233 B1 | 4/2003 | Fukui et al. | |
| 6,709,149 B1 | 3/2004 | Tepic | |
| 6,869,284 B2 | 3/2005 | Aoyagi et al. | |
| 6,935,541 B1 | 8/2005 | Campbell et al. | |
| 7,073,936 B1 | 7/2006 | Jonsson | |
| 8,128,276 B2 | 3/2012 | Axelsson et al. | |
| 8,690,419 B2 | 4/2014 | Faccioli et al. | |
| 8,747,866 B2 | 6/2014 | Vogt et al. | |
| 8,757,866 B2 | 6/2014 | Vogt et al. | |
| 8,968,000 B2 | 3/2015 | Leiner et al. | |
| 9,247,979 B2 | 2/2016 | Faccioli et al. | |
| 9,326,829 B2 | 5/2016 | Kojima et al. | |
| 9,775,690 B2 | 10/2017 | Cheetham | |
| 2003/0012079 A1 | 1/2003 | Coffeen | |
| 2004/0074927 A1 | 4/2004 | Lafond | |
| 2004/0122359 A1 | 6/2004 | Wenz | |
| 2005/0128868 A1 | 6/2005 | Vries | |
| 2005/0222538 A1 | 10/2005 | Embry et al. | |
| 2006/0274601 A1 | 12/2006 | Seaton | |
| 2012/0155214 A1 | 6/2012 | Faccioli | |
| 2013/0090596 A1 | 4/2013 | Asai | |
| 2014/0110356 A1 | 4/2014 | McKay | |
| 2014/0192611 A1 | 7/2014 | Sasaki et al. | |
| 2014/0254303 A1 | 9/2014 | McArthur et al. | |
| 2014/0269147 A1 | 9/2014 | Click et al. | |
| 2015/0329339 A1 | 11/2015 | Oberli | |
| 2016/0045283 A1 | 2/2016 | Boehm et al. | |
| 2017/0252715 A1 | 9/2017 | Vogt et al. | |
| 2018/0132917 A1 | 5/2018 | Vogt et al. | |
| 2018/0132919 A1 | 5/2018 | Vogt et al. | |
| 2018/0256233 A1 | 9/2018 | Vogt et al. | |
| 2018/0289406 A1 | 10/2018 | Vogt et al. | |
| 2018/0310974 A1 | 11/2018 | Vogt et al. | |
| 2018/0333176 A1 | 11/2018 | Vogt et al. | |
| 2019/0216516 A1 | 7/2019 | Vogt et al. | |
| 2020/0129215 A1 | 4/2020 | Vogt | |
| 2020/0129216 A1 | 4/2020 | Vogt | |
| 2020/0179023 A1 | 6/2020 | Vogt et al. | |

FOREIGN PATENT DOCUMENTS

| | | |
|---|---|---|
| DE | 69812726 | 2/2004 |
| DE | 20 2005 010 206 | 9/2005 |
| DE | 10 2009 031 178 | 9/2010 |
| DE | 102009031178 | 9/2010 |
| DE | 102016121607 | 5/2018 |
| DE | 10 2018 101 041 | 7/2019 |
| EP | 0 692 229 | 1/1996 |
| EP | 0692229 | 1/1996 |
| EP | 0 796 653 | 9/1997 |
| EP | 0796653 | 9/1997 |
| EP | 1 005 901 | 6/2000 |
| EP | 1005901 | 6/2000 |
| EP | 1 016 452 | 7/2000 |
| EP | 1 020 167 | 7/2000 |
| EP | 1016452 | 7/2000 |
| EP | 1020167 | 7/2000 |
| EP | 1093826 | 4/2001 |
| EP | 1 886 647 | 2/2008 |
| EP | 1886647 | 2/2008 |
| EP | 1883379 | 9/2013 |
| EP | 3320870 | 5/2018 |
| JP | 2011-067265 | 4/2011 |
| WO | 94/26403 | 11/1994 |
| WO | 99/67015 | 12/1999 |
| WO | 00/35506 | 6/2000 |
| WO | 2006/123205 | 11/2006 |
| WO | 2011/089480 | 7/2011 |
| WO | 2012/115022 | 8/2012 |

OTHER PUBLICATIONS

Non-Final Office Action dated Aug. 10, 2021 in U.S. Appl. No. 16/655,610.
Charnley, J., "Anchorage of the Femoral Head Prosthesis of the Shaft of the Femur," The Journal of Bone and Joint Surgery, 42 B, No. 1, pp. 28-30 (Feb. 1960).
Kühn, Klaus-Dieter, "Bone Cements," Springer-Verlag, pp. 9 (2000).
Non-Final Office Action dated Jul. 29, 2021 in U.S. Appl. No. 16/705,881.

* cited by examiner ically is a25the starting components required for production of the bone
DEVICE FOR MIXING A BONE CEMENT WITH HOLLOW SPACE FOR MONOMER TRANSFER

CROSS-REFERENCE TO RELATED APPLICATION

This Utility Patent Application claims priority to German Application No. 10 2018 131 268.7 filed on Dec. 7, 2018, which is incorporated herein by reference.

TECHNICAL FIELD

One embodiment relates to a device for production of a bone cement dough from a monomer liquid and a cement powder as starting components of the bone cement dough, and for dispensing of the mixed bone cement dough.

One embodiment also relates to a method for production of a bone cement dough, in particular of a pasty polymethylmethacrylate bone cement dough, with the device.

BACKGROUND

The subject matter of one embodiment specifically is a device for separate storage of the cement powder and the monomer liquid of polymethylmethacrylate bone cements, for subsequent mixing of the cement powder with the monomer liquid in order to produce a bone cement dough, and for dispensing the mixed bone cement dough. In one embodiment, the device is a full-prepacked mixing system. Particularly in one embodiment, the device is designed appropriately such that mixed bone cement dough can be dispensed without the use of a separate extrusion device.

Polymethylmethacrylate (PMMA) bone cements are based on the pioneering work of Sir Charnley (Charnley, J.: Anchorage of the femoral head prosthesis of the shaft of the femur. J. Bone Joint Surg. 42 (1960) 28-30.). Conventional polymethylmethacrylate bone cements (PMMA bone cements) are made from a powdered component and a liquid monomer component (K.-D. Kühn: Knochenzemente für die Endoprothetik: Ein aktueller Vergleich der physikalischen und chemischen Eigenschaften handelsüblicher PMMA-Zemente. Springer-Verlag Berlin Heidelberg New York, 2001). The monomer component generally contains the monomer, methylmethacrylate, and an activator (N,N-dimethyl-p-toluidine) dissolved therein. The powder component, also called cement powder or bone cement powder, includes one or more polymers that are produced through polymerisation, in one embodiment suspension polymerisation, based on methylmethacrylate and co-monomers, such as styrene, methylacrylate or similar monomers, a radiopaquer, and the initiator, dibenzoylperoxide. Mixing the powder component and the monomer component, swelling of the polymers of the powder component in the methylmethacrylate generates dough that can be shaped plastically and is the actual bone cement or bone cement dough. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the bone cement dough increases until the bone cement dough solidifies.

PMMA bone cements can be mixed by mixing the cement powder and the monomer liquid in suitable mixing beakers with the aid of spatulas. This can lead to air bubbles being enclosed in the bone cement dough, which can have a negative effect on the mechanical properties of the cured bone cement.

A large number of vacuum cementing systems has been described for preventing air inclusions in bone cement dough of which the following shall be specified here for exemplary purposes: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, U.S. Pat. No. 5,344,232 A.

Cementing systems, in which both the cement powder and the monomer liquid are already packed in separate compartments of the mixing devices and are mixed with each other in the cementing system only right before application of the cement, are a development of cementing technology. Said closed full-prepacked mixing systems have been proposed in EP 0 692 229 A1, DE 10 2009 031 178 B3, U.S. Pat. Nos. 5,997,544 A, 6,709,149 B1, DE 698 12 726 T2, EP 0 796 653 A2, U.S. Pat. No. 5,588,745 A, US 2018/333 176 A1, US 2018/310 974 A1, US 2018/289 406 A1, US 2018/132 919 A1, US 2018/132 917 A1, and US 2018/256 233 A1.

Patent DE 10 2009 031 178 B3 discloses a storage and mixing device as a full-prepacked mixing system, in which the starting components required for production of the bone cement dough are stored already in the storage and mixing device and can be combined and mixed in the storage and mixing device. The storage and mixing device includes a two-part dispensing plunger for closing a cement cartridge. A combination of a gas-permeable sterilisation plunger and a gas-impermeable sealing plunger is used in this context.

After mixing the cement powder with the liquid monomer component, polymethylmethacrylate bone cements are applied in their non-cured pasty state in the form of a bone cement dough. If mixing devices are used with powder-liquid cements, the bone cement dough is situated in a cartridge. During the application of said conventional PMMA bone cements, the bone cement dough produced after mixing the two starting components is extruded with the aid of manually operable extrusion devices. The bone cement dough is squeezed from said cartridge by moving a dispensing plunger.

These simple mechanical extrusion devices utilise, in particular, clamp rods that are driven by a manually-actuated tilting lever for extrusion. The manually driven extrusion devices are time-proven throughout the world for decades and as such are the current prior art. Said extrusion devices are advantageous in that the medical user has a feel for the penetration resistance of the bone cement dough into the bone structures (cancellous bone) by means of the manual force to be expended.

The use of many full-prepacked mixing systems known to date requires the medical user to perform multiple working steps on the devices in a predetermined order, one after the other, until the bone cement dough is ready-mixed and can be applied. Any confusion of the working steps can lead to failure of the mixing device and can therefore cause a disturbance in the surgical procedure. Cost-intensive training of the medical users is therefore required in order to prevent user errors from occurring.

WO 00/35506 A1 proposes a device, in which polymethylmethacrylate cement powder is stored in a cartridge, whereby the cement powder takes up the entire volume of the cartridge and the volume of the intervening spaces between the particles of the cement powder is equal to the volume of the monomer liquid required for the production of bone cement dough with the cement powder stored in the cartridge. The design of said device is appropriate such that the action of a vacuum causes the monomer liquid to be conducted into the cartridge from above, whereby a vacuum is applied to a vacuum connector on the underside of the cartridge for this purpose. As a result, the monomer liquid is aspirated through the cement powder, whereby the air present in the intervening spaces of the cement powder particles is displaced by the monomer liquid. This involves no mechanical mixing of the cement dough thus formed by means of a stirrer.

It is a disadvantage of the system that cement powders, which swell quickly due to the monomer liquid, cannot be mixed with said device, because the rapidly swelling cement powder particles form a gel-like barrier of approximately 1 to 2 cm after ingress of the monomer liquid into the cement powder and impede the migration of the monomer liquid through the entire cement powder. Moreover, conventional cement powders illustrate a phenomenon, which is that the cement powder particles are wetted only poorly by methylmethacrylate due to the difference in surface energies. As a result, the methylmethacrylate penetrates only slowly into the cement powder. Moreover, it cannot be excluded that the monomer liquid, exposed to the action of a vacuum, is aspirated through the vacuum connector after the monomer liquid fully penetrates into the cement powder. In this case, an insufficient amount of monomer liquid for curing by means of radical polymerisation is available and/or the mixing ratio and thus the consistency of the bone cement is changed inadvertently. Moreover, it is a problem that the air trapped between the cement powder particles is to be displaced by the monomer liquid proceeding from top to bottom, because the air, having a lower specific weight than the monomer liquid, tends to migrate upwards in the cement powder rather than downwards in the direction of the vacuum connector under the force of gravity.

From the adhesives and sealant industry, electrically driven extrusion devices are known as well. Said devices can be driven both with rechargeable batteries and batteries or by means of a stationary electrical power supply. Said devices can extrude particularly thick pasty masses since their extrusion force is very large in some cases. However, it is one disadvantage of the use of electrical motors that these motors contain non-ferrous metals and are expensive purchases. Since the OR area needs to be kept sterile, said devices need to be sterilised with much effort or may even need to be replaced. The presence of electrical wiring may impede the mobility of the user in the OR.

Moreover, pneumatic devices have been proposed as well. Said devices require a stationary or mobile compressed air connection (U.S. Pat. No. 2,446,501 A, DE 20 2005 010 206 U1). This necessitates compressed air hoses, which may impede the mobility of the user.

Alternatively, the use of compressed gas cartridges to provide compressed gas is feasible just as well. Devices have been proposed for this purpose, in which the supply of compressed gas is controlled by a valve and, in addition, the flow of the viscous mass is controlled by a second valve (US 2004/0074927 A1, U.S. Pat. No. 6,935,541 B1). These devices have the gas cartridges integrated into the devices. These systems, which are connected to compressed air or contain compressed gas cartridges, always necessitate the presence of a compressed gas source in the absence of which the systems cannot be used.

US 2018/132 917 A1 and US 2018/132 919 A1 proposed full-prepacked mixing systems with a cartridge containing a bone cement powder. A dispensing plunger is provided in the cartridge and a receptacle containing a monomer liquid container is arranged downstream from the cartridge. A conveying plunger is situated on the rear side of the receptacle and can be used to crush the monomer liquid container and to extrude the monomer liquid from the receptacle into the cartridge. In this mixing system, monomer liquid is pressed into compacted cement powder, whereby the cement powder become wetted by the monomer liquid and the air present between the cement powder particles is pressed out by the monomer liquid. This means, a bubble-free cement dough is generated without the action of mechanical mixing devices. For the mixing system to work properly, it is indispensable to connect a separate mechanical extrusion device to the cartridge system. By manual actuation of the extrusion device, the monomer liquid container is opened first, then the monomer liquid is pressed into the cement powder, whereby the cement dough is generated. Subsequently, further actuation of the extrusion device excludes the cement dough thus formed from the cartridge. It is currently customary to use extrusion devices that can be resterilised and need to be cleaned and sterilised after use.

SUMMARY

It is the object of the present embodiments to overcome the disadvantages of the prior art. Specifically, it is the object of one embodiment to develop a device that is intended and well-suited for the mixing of the bone cement dough from the starting components, as well as to develop a method for production of a bone cement dough, in particular of a pasty polymethylmethacrylate bone cement dough, whereby the bone cement dough is produced with a device of this type from a cement powder and a monomer liquid, by means of which the drawbacks of the previous devices and methods are overcome. It is the object of one embodiment to improve a device like the ones according to US 2018/132 917 A1 and US 2018/132 919 A1 such that an amount of monomer liquid that can be predetermined can be pressed into the cement powder, if at all possible without trapping gas or air. Accordingly, what is to be attained with the device according to one embodiment and the method according to one embodiment is that a homogeneous bone cement dough can be generated and applied throughout the entire extrusion process even with the device being very simple and inexpensive in design and the device also being very easy and simple to use.

It shall be feasible to drive the device without an extrusion device, and the device is to be as easy as possible to operate. The design is to be inexpensive to allow the device to be used just a single time for hygienic reasons. As many as possible or all of the processes taking place in the device, such as the mixing of the starting components, the dispensing of the bone cement dough, and, if applicable, the opening of the monomer liquid container and, if applicable, the opening of the cartridge, are to take place in the smallest possible number of working steps and are to be automated to the extent possible and in one embodiment are to be driven by a single linear drive only.

Accordingly, the development of a device for the mixing of cement powder and monomer liquid is also the object of one embodiment. The handling of the device is to be maximally simplified in order to basically prevent operating errors resulting from installation steps taking place incorrectly. It should be feasible for the medical user to actuate the device directly after removing it from a packaging. Assembly and working steps are to be omitted due to the design of the device. It shall be possible to store cement powder and monomer liquid separate from each other in the device. The device is preferred to be a full-prepacked mixing system. It shall be feasible to mix the two cement components within few seconds in the closed device without any manual mixing with mixing wheels and/or mixing vanes being required. In this context, the mixing is to be appropriate such that the medical user does not contact the cement powder and the monomer liquid. Moreover, the mixing system shall be appropriate such that no assembly steps and no external vacuum are required for monomer transfer. The mixing system to be developed shall allow the cement dough produced after the two cement components have been mixed to be extruded without connecting an external extrusion device, in one embodiment through manual actuation of the device itself. The device shall allow polymethylmethacrylate bone cement dough to be prepared and applied without requiring any additional equipment, such as vacuum sources, vacuum hoses, and extrusion devices. Moreover, the monomer liquid shall be transferred appropriately such that only monomer liquid with no gas inclusions and/or air bubbles rather than a mixture of air and monomer liquid is transferred into the cement powder. This shall prevent a formation of air inclusions in the bone cement dough. The device is in one embodiment designed to be a stand-up system such that the device can be placed perpendicular on a table and such that the entire procedure of the transfer of the monomer liquid into the cement powder and the mixing of the cement powder with the monomer liquid and, if applicable, the opening of the monomer liquid container can take place in this position without any change of position of the device being required.

In one embodiment, the device is to also ensure the secure storage of cement powder and monomer liquid in separate compartments such that any inadvertent mixing of the cement components during storage of the device is excluded. The device is to allow for sterilisation with ethylene oxide gas. For this purpose, the cement powder stored in the device must be accessible to ethylene oxide.

The objects of one embodiment are met by a device for production of a bone cement dough from a monomer liquid and a cement powder as starting components of the bone cement dough, and for dispensing of the bone cement dough, the device comprising 1) a cartridge with a cylindrical internal space;
2) a cartridge head with a dispensing opening for dispensing the bone cement dough, whereby the cartridge head closes the cartridge on a front side of the cartridge except for the dispensing opening;
3) a conveying plunger that is arranged in the internal space of the cartridge and is stored in the internal space of the cartridge such that it is pushable in the direction of the dispensing opening;
4) a dispensing plunger that is arranged in the internal space of the cartridge between the dispensing opening and the conveying plunger and that is supported in the internal space of the cartridge such that it is pushable in the direction of the dispensing opening;
5) a first hollow space that is bordered by the cartridge head, by internal walls of the cartridge, and by the dispensing plunger, whereby the cement powder is arranged in the first hollow space;
6) a second hollow space that is part of the cylindrical internal space of the cartridge, whereby the second hollow space is bordered by the dispensing plunger and the conveying plunger;
7) a fluid opening that is arranged in the conveying plunger and through which the monomer liquid is conveyable into the second hollow space;
8) a feedthrough that is arranged in the dispensing plunger and/or in the wall of the cartridge and which connects the first hollow space and the second hollow space in monomer liquid-permeable, but cement powder-impermeable manner, and
9) a closure means that is arranged on a rear side of the dispensing plunger that faces away from the dispensing opening, whereby the closure means projects away from the dispensing plunger in the direction of the conveying plunger and is situated at a distance from the fluid opening in the conveying plunger, whereby the fluid opening is closable with the closure means when the conveying plunger is being pushed in the direction of the dispensing opening, and whereby the closure means is appropriately mobile in the fluid opening closed by the closure means such that the fluid opening stays closed, while the conveying plunger is pushable further in the direction of the dispensing plunger.

BRIEF DESCRIPTION OF DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Further exemplary embodiments shall be illustrated in the following on the basis of eleven schematically depicted figures, though without limiting the scope of the embodiments. In the figures.

DETAILED DESCRIPTION

Figure 1:
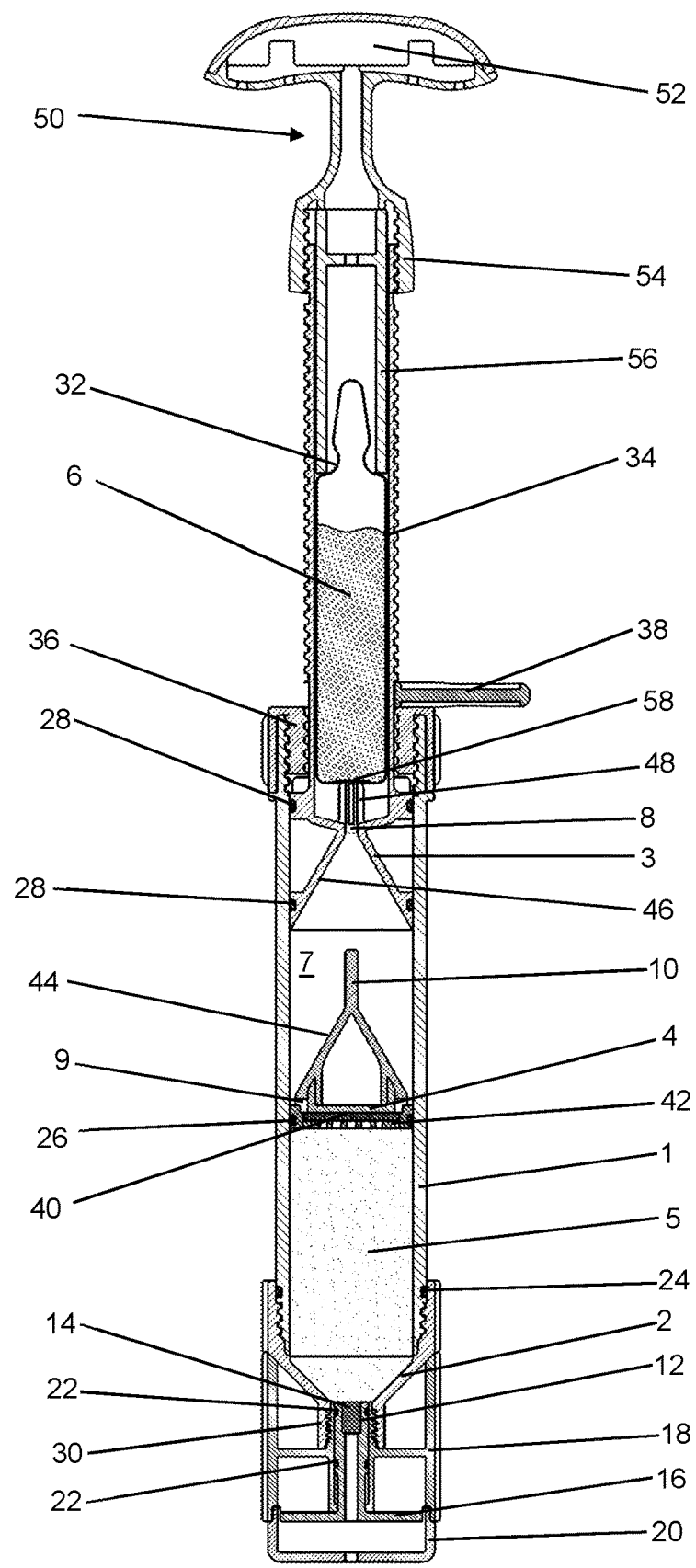
FIG. 1: illustrates a schematic cross-sectional view of a first exemplary device according to one embodiment for storage and mixing of a monomer liquid and a cement powder in a starting state and/or storage state of the device.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

One embodiment can just as well provide a further fluid opening to next to the fluid opening for the same purpose. For this purpose, one embodiment can provide at least one additional closure means by means of which the at least one further fluid opening is closable to be arranged next to the closure means on the rear side of the dispensing plunger. In this context, the at least one further fluid opening and the at least one additional closure means can, wherever possible, include the advantages and properties illustrated in the following that are assigned to the fluid opening and/or the closure means.

It shall be noted expressly that the bone cement dough can be dispensed from the device onto a spatula or into a vessel for later use. Direct application on a patient is therefore not required.

In one embodiment, the fluid opening is closable by the closure means in fluid-tight manner, particularly in one embodiment it is closable in fluid-tight and gas-tight manner.

While the conveying plunger is pushed further in the direction of the dispensing plunger and the closure means closes the fluid opening, the second hollow space may progressively decrease in size.

In one embodiment, the device is also designed for storage of the cement powder and particularly in one embodiment for storage of the monomer liquid as well.

One embodiment can provide a dispensing tube to be attachable to the front side of the cartridge, in particular to the cartridge head, whereby the dispensing tube particularly in one embodiment borders the dispensing opening.

The internal space of the cartridge has a cylindrical geometry. The cylindrical shape is the simplest shape by means of which the internal space of the cartridge can be implemented. A cylindrical shape shall be understood geometrically to mean the shape of a general cylinder of any footprint, i.e. not just a cylinder having a circular footprint. Accordingly, the internal wall of the internal space of the cartridge can be realised by means of the cylinder jacket of a cylinder of any footprint, in particular of different footprints, including non-circular or non-round footprints. However, according to one embodiment, a cylindrical geometry with a rotationally symmetrical and, in particular, circular footprint is preferred for the internal space, since these are the easiest to manufacture.

One embodiment can provide a front side of the conveying plunger that faces the dispensing plunger and the rear side of the dispensing plunger to be shaped with matching surfaces with respect to each other such that the front side of the conveying plunger touches against the rear side of the dispensing plunger with matching surfaces, when the conveying plunger is pushed against the dispensing plunger, whereby in one embodiment the volume of the second hollow space thereby is reducible to a maximum of 1% of the volume of the second hollow space in a starting state, whereby the at least one closure means is situated at a distance from the at least one fluid opening in the starting state.

As a result, all or a large fraction of a monomer liquid conducted into the second hollow space can be pressed into the first hollow space by pushing the conveying plunger in the direction of the dispensing plunger while the fluid opening is already closed.

Moreover, one embodiment can provide a front side of the conveying plunger that faces the dispensing plunger to include a surface that tapers continuously in the direction of the fluid opening, and the rear side of the dispensing plunger to include a surface that matches it like a negative shape and tapers continuously in the direction of the closure means.

This prevents projections or undercuts from forming in the second hollow space, which would enable or provoke the formation of air inclusions in the monomer liquid conducted into the second hollow space when the device is set up vertically with the cartridge head downwards.

Moreover, one embodiment can provide a front side of the conveying plunger that faces the dispensing plunger to include a depression with a funnel-shaped surface whose lowest point has the fluid opening arranged in it, and can provide the rear side of the dispensing plunger to include a projecting, cone-shaped surface of the same slope as the funnel-shaped surface, whereby the closure means is arranged on the tip of the cone-shaped surface.

By this means, not only can the formation of gas or air inclusions in the second hollow space be prevented, but gas or air inclusions can easily escape through the fluid opening while the monomer liquid is filled into the second hollow space.

In this context, one embodiment can provide the funnel-shaped surface on the front side of the conveying plunger to include an angle of slope of at least 45°, in one embodiment of at least 55°, in one embodiment of at least 60°, and the cone-shaped surface on the rear side of the dispensing plunger to include a matching angle of slope of at least 45°, in one embodiment of at least 55°, in one embodiment of at least 60°.

This enables the rapid escape of gas inclusions from the second hollow space when the device is set up vertically with the cartridge head downwards.

One embodiment can just as well provide the closure means to be a cylindrical rod that projects away from the rear side of the dispensing plunger by a length of at least 10 mm.

This ensures that the second hollow space is large enough for a sufficiently large amount of the monomer liquid being pressed into it.

One embodiment can provide the dispensing plunger and/or the conveying plunger to be sealed with respect to an internal wall of the cartridge, whereby the internal wall of the cartridge is a boundary of the internal space of the cartridge. In this context, one embodiment can provide the dispensing plunger and/or the conveying plunger to be sealed with respect to the internal wall of the cartridge by at least one sealing ring. In this context, one embodiment can, in turn, particularly in one embodiment provide the at least one sealing ring to be arranged in at least one circumferential groove in the dispensing plunger and/or conveying plunger.

The sealing prevents the monomer liquid from possibly being pushed such as to bypass the dispensing plunger and/or the conveying plunger and from thus having an adverse influence on the desired mixing ratio or causing contamination of the surroundings.

According to a particularly preferred development, one embodiment can provide a container to be arranged on a rear side of the conveying plunger that faces away from the dispensing plunger, with a monomer liquid container containing the monomer liquid being arranged in the container, in particular an ampoule made of glass or plastics, whereby the monomer liquid container is openable inside the container and whereby the container is connected to the second hollow space in fluid-permeable manner via the fluid opening, whereby an opening means is in one embodiment arranged on a side of the container opposite from the conveying plunger, by means of which the monomer liquid container is openable inside the container, whereby the opening means is particularly preferred to be a sleeve attached to a cap, whereby the cap is screwable onto a thread of the container and the cap includes a counter-thread for this purpose such that, when the cap is being screwed on, the monomer liquid container, in particular the ampoule, is pushed, by the sleeve, onto at least one projecting pin on the internal side of the container and thus the monomer liquid container, in particular the ampoule, is breakable open.

By this means, a full-prepacked mixing system is provided, in which all starting components of the bone cement dough, namely the monomer liquid and the cement powder, can be stored and mixed in the device. The handling of the monomer liquid can thus take place inside the device and the user is protected from the cement powder and, in particular, from the monomer liquid.

In one embodiment, the closure means is situated on the same axis as the container for the monomer liquid container.

In one embodiment, the monomer liquid container is plugged into a fit in the container such that the monomer liquid container is being held in the container. A screen or a filter for retention of fragments of the monomer liquid container can be arranged at the merging site to the fluid opening in the container.

The sleeve can be a piece of tubing. The sleeve can push onto the shoulders of an ampoule as monomer liquid container such that the ampoule is pushed open on an ampoule base of the ampoule in the container. In one embodiment, the sleeve and the cap are a single part or form a unit.

In one embodiment, glass ampoules, plastic ampoules, plastic bags, film bags, plastic compound bags, and aluminium-plastic compound bags that are suitable for storing monomer liquid can be used as monomer liquid container.

Moreover, one embodiment can just as well provide a ventilation opening connecting the internal space of the container to the surroundings to be arranged in the wall of the container or in the opening means.

By this means, the internal space of the container can easily be evacuated and sterilised with a sterilising gas.

According to a preferred development, one embodiment can just as well provide the at least one ventilation opening to be arranged so close in the vicinity of a screw cap, in particular of a screw cap as opening means for opening a monomer liquid container, in the container such that the at least one ventilation opening is closed through a motion of the screw cap in the direction of the cartridge before a monomer liquid container that contains the monomer liquid and is arranged in the container is being opened through the motion of the screw cap.

By this means, the monomer liquid cannot exit from the internal space of the container, when the at least one ventilation opening is closed by the screw cap moving in the direction of the cartridge before the monomer liquid container is opened through the motion of the screw cap, i.e. for example is squashed, splintered, punctured or torn open in the internal space of the container.

In devices according to one embodiment having a container, one embodiment can provide the container to include an external thread that is screwable into an internal thread on an end of the cartridge opposite from the cartridge head, whereby the conveying plunger is pushable in the direction of the dispensing opening by screwing the container into the cartridge and the dispensing plunger is pushable by the conveying plunger in the direction of the dispensing opening, whereby the internal thread in one embodiment is part of a ring sleeve that is connected to the cartridge on the end of the cartridge opposite from the cartridge head.

By this means, the device can be operated from outside through a screw motion. The screw motion is advantageous in one embodiment in that a forceful propulsion of the conveying plunger and dispensing plunger is enabled such that even viscous bone cement doughs can be extruded from the cartridge with the device.

One embodiment can just as well provide that the closure means is pushable into the container through the fluid opening. For this purpose, the closure means can have a greater length in order to close the second hollow space early on with respect to the fluid opening such that a sufficiently large amount of the monomer liquid is pushable from the second hollow space into the first hollow space in order to attain the desired consistency of the bone cement dough.

One embodiment can also provide the length of the closure means to be appropriate such that the volume of the second hollow space is at most equal to the volume of the monomer liquid conducted through the fluid opening, in particular of the monomer liquid contained in the monomer liquid container, when the tip of the closure means encounters and closes the fluid opening.

By this means, gases can exit from the second hollow space such that the second hollow space contains only the monomer liquid when the closure means closes the fluid opening.

Moreover, one embodiment can provide the closure means to be cylindrical in shape and the fluid opening to have a matching shape, whereby the closure means in one embodiment has a cylindrical shape with a circular footprint and the fluid opening is a circular or cylindrical hole.

This ensures that the closure means can reliably close the fluid opening in any position.

Moreover, one embodiment can just as well provide a stopper to be arranged in the dispensing opening, with the stopper closing the dispensing opening impermeable to the cement powder, in particular closing the dispensing opening permeable to gases, whereby the stopper in one embodiment is arranged in the dispensing opening such as to be mobile such that the stopper is pushable out of the dispensing opening by pressing on the ready-mixed bone cement dough, whereby it is particularly preferred to have a marker means that is visible from outside attached to the stopper, whose position is readable from outside to indicate whether the stopper is pushed outward in the dispensing opening.

By this means, premature leakage of the bone cement dough can be prevented. The preferred embodiment allows it to be recognised from outside when the bone cement dough is ready-mixed up to the dispensing opening. This is the result of the bone cement dough being flowable, while the cement powder is not flowable, such that the stopper is moved only if the bone cement dough is ready-mixed or if the cement powder is at least completely wetted and the dispensing plunger exerts a pressure on the stopper via the bone cement dough.

The stopper can be part of a closure system closing the dispensing opening. In this context, the stopper can be arranged in a cylindrical borehole of the closure system such as to be mobile in axial direction. The closure system is screwable into an internal thread on a socket of the cartridge head by means of an external thread. Obviously, the closure system can alternatively just as well include a cap with an internal thread that is screwed onto a socket on the cartridge head with an external thread. After removing the closure system, the socket can be connected to a dispensing tube.

The marker means is preferred to be a coloured ring.

One embodiment can just as well provide for a detachably attached foot to be arranged on the cartridge head, whereby the foot is preferred to be at least partially transparent, whereby it is particularly preferred for a part of the foot facing the cartridge head is to be non-transparent and a part of the foot facing away from the cartridge head to be transparent.

By this means, the device can conveniently be set up in the desired position, namely with the cartridge head downwards.

The marker means is in one embodiment arranged in the foot. It is preferred in this context for the marker means to be arranged in the non-transparent part of the foot while the mixing of the monomer liquid with the cement powder is not yet completed. By pressing on the ready-mixed bone cement dough, the marker means is pushable into the transparent part of the foot such that it can be visually recognised from outside through the foot when the bone cement dough is ready for use.

The cartridge is preferred to be hollow cylinder-shaped. The cartridge head can be conical in shape. As a result, a dead volume remains inside the cartridge head, when the dispensing plunger is pushed up to the cartridge head. Less well-mixed fractions of the bone cement dough that cannot be dispensed can be retained in this place.

The feedthrough is in one embodiment arranged on the tip or in the envelope of a cone on the rear side of the dispensing plunger.

The closure means is in one embodiment shaped to be cylindrical, whereby the external diameter of the closure means is equal to or larger than the internal diameter of the fluid opening. By this means, the closure means can reliably close the fluid opening regardless of how deeply the closure means is pushed into the fluid opening.

One embodiment can just as well provide the volume of the monomer liquid used here, in particular the volume of the monomer liquid contained in the monomer liquid container, to be at least equal to the volume of the second hollow space.

One embodiment can provide the cement powder to be appropriately compacted in the first hollow space such that the cement powder particles are not freely mobile. This ensures that the monomer liquid can spread rapidly and homogeneously in the cement powder due to capillary forces.

One embodiment can provide a detachable locking means preventing a motion of the conveying plunger against the cartridge to be connected to the conveying plunger. In one embodiment, the locking means is arranged on the container for the monomer liquid container and blocks the container from being pushed or screwed into the cartridge and thus blocks a motion of the conveying plunger in the cartridge.

The cartridge is in one embodiment manufactured from a thermoplastic material, in particular with an injection moulding procedure. It is particularly preferred for the other parts of the device, such as the dispensing plunger, the conveying plunger, and the cartridge head, as well as, if applicable, the container, the stopper, and the foot, to also be manufactured from a thermoplastic material, in particular with an injection moulding procedure.

The underlying objects of the present embodiments are also met by a method for the production of a bone cement dough, in particular a pasty polymethylmethacrylate bone cement dough, whereby the bone cement dough is produced from a cement powder and a monomer liquid with a device according to embodiments as described above, characterized by the following steps proceeding in the order given:
  A) conducting the monomer liquid through the fluid opening into the second hollow space;
  B) pushing the conveying plunger in the direction of the dispensing plunger until the closure means on the rear side of the dispensing plunger closes the fluid opening;
  C) pushing the conveying plunger further in the direction of the dispensing plunger, whereby the monomer liquid is pushed from the second hollow space into the cement powder in the first hollow space, with the closure means being pushed through the fluid opening or more deeply into the fluid opening and the fluid opening remaining closed;
  D) the conveying plunger pushing the dispensing plunger in the direction of the dispensing opening, whereby the bone cement dough produced in the first hollow space flows out through the dispensing opening.

One embodiment can provide no treatment of a human or animal body to take place in the method according to one embodiment, in particular no treatment of a human or animal body that is excluded from patenting to take place.

Moreover, one embodiment can provide for the bone cement dough to be produced in the first hollow space during step C) and/or after step C), but before step D).

One embodiment can just as well provide for the device to be set up or held with the cartridge head downwards in step A), and in one embodiment in steps B) and C) as well, and for gas inclusions to escape from the second hollow space through the fluid opening.

By this means, an exactly predetermined amount of the monomer liquid can be introduced into the cement powder. Moreover, a bone cement dough that is free or depleted of bubbles can be produced by this means.

However, it is not a tragedy if a small amount of air inclusions remains in the second hollow space, in particular if these remain in the feedthrough between the first hollow space and the second hollow space and do not enter into the first hollow space.

Moreover, one embodiment can provide the conveying plunger to touch against the dispensing plunger with matching surfaces in step D), and in one embodiment the volume of the second hollow space to be reduced, in step C), completely to zero or down to a maximum of 1% of the volume of the second hollow space in a starting state.

By this means, the monomer liquid can be pressed completely from the second hollow space into the cement powder in the second hollow space.

Moreover, one embodiment can provide the pressure acting on the bone cement dough in step D) to move or push forward a stopper in the dispensing opening, whereby the stopper is in one embodiment removed from the dispensing opening subsequently and, if applicable, a foot is removed from the cartridge head and, particularly in one embodiment, then an application tube is attached to the cartridge head of the cartridge.

This allows a user of the device to recognise when the bone cement dough is ready for use.

One embodiment can just as well provide for a monomer liquid container containing the monomer liquid to be opened in a container before step A) and the monomer liquid is released in the container, whereby the container is arranged on a rear side of the conveying plunger that faces away from the dispensing plunger, and the monomer liquid flows from the container through the fluid opening into the second hollow space in step A), whereby, in one embodiment, the conveying plunger in steps B) and C) and the conveying plunger and the dispensing plunger in step D) are driven by the container being pushed or screwed into the cartridge.

This allows the method to be implemented easily by hand. The device can be used as full-prepacked mixing system and any contact of the user with the monomer liquid during the method can be excluded.

One embodiment is based on finding, surprisingly, that having a fluid opening in a conveying plunger that is closable by a dispensing plunger allows a hollow space (the second hollow space presently) to be closed with respect to the outside through a motion of the conveying plunger relative to the dispensing plunger and thus to provide a monomer liquid reservoir that is closed towards the outside, but is connected in the direction of a (first) hollow space containing the cement powder such as to be permeable to the monomer liquid, whereby the monomer liquid reservoir is pushable into the cement powder through a further motion of the conveying plunger towards the dispensing plunger, whereby the second hollow space is progressively reduced in size in the process and whereby the monomer liquid reservoir is free or essentially free of gas and/or air inclusions provided the device is set up appropriately. In order to push the monomer liquid contained in the second hollow space into the cement powder and in order to extrude the ready-made bone cement dough, it is sufficient to push the conveying plunger in the direction of the dispensing opening. In the process, the fluid opening closes first, then the monomer liquid is transferred into the first hollow space with the cement powder and subsequently the bone cement dough thus produced can be expelled from the cartridge by propelling the conveying plunger jointly with the dispensing plunger.

In one embodiment, the monomer liquid can beforehand be conducted from a container, which is attached to the rear side of the conveying plunger and is connected to the fluid opening, through the fluid opening into the second hollow space. In this context, the conveying plunger is pushable in the internal space of the cartridge in the direction of the dispensing opening through inserting and/or screwing the container into the cartridge. Particularly in one embodiment, a monomer liquid container is openable within the container beforehand in order to release the monomer liquid within the container. The essential advantages of said particularly preferred device according to one embodiment are that the two starting components of the bone cement dough are stored in the closed cementing system and that the mixing of the starting components takes place in the closed device. This means that the user does not need to fill the device. This then constitutes a full-prepacked mixing system. The medical user is not at all exposed to the individual starting components of the bone cement dough. As a result, the unpleasant odour is minimised.

It is a particular advantage of the device in one embodiment is that the monomer liquid is pressed into the cement powder by simply moving the conveying plunger forward while the fluid opening stays closed. In the process, the air present between the cement powder particles is displaced by the monomer liquid. A homogeneous bone cement dough is produced without any need for any manual mixing with mixing rods with mixing vanes. This means that the error-prone manual mixing is no longer required. This requires the use of a cement powder that is adjusted appropriately such that it is wetted very well by the monomer liquid and can aspirate the monomer liquid through capillary action. The operation of the device is maximally simplified.

The advantages of devices and methods according to embodiments are basically based on generally known linear motions being utilised to perform the monomer transfer and to close the second hollow space towards the outside.

The device can be used as a hygienic disposable product since it can be manufactured largely from plastics and since all parts including the internal spaces and the cement powder can be sterilised with ethylene oxide.

An exemplary and preferred device according to one embodiment for the storing, mixing, and dispensing of polymethylmethacrylate bone cement can include:
a) a hollow cylinder-shaped cartridge;
b) a cartridge head that closes the cartridge, whereby the cartridge head includes an outlet opening that connects the internal space of the cartridge to the surroundings;
c) a gas-permeable and powder particle-impermeable stopper as cartridge closure that is detachably arranged in the outlet opening of the cartridge head, whereby the cartridge closure is connected to a foot;
d) a dispensing plunger that is arranged in the internal space of the cartridge such as to be axially mobile, whereby at least a part of the rear side of the dispensing plunger is provided in the form of a cone, whereby at least one opening as feedthrough is provided at or near the envelope of the cone, and is impermeable to powder particles and permeable to gases and liquids, and connects the front side and the rear side of the dispensing plunger in gas- and liquid-permeable manner;
e) a hollow cylinder-shaped ampoule holder as container that is arranged, at least partially, in the internal space of the cartridge and is axially mobile in the cartridge, whereby the ampoule holder is provided, on its front face facing the cartridge head, as conveying plunger in the form of a hollow cone (funnel-shaped);
f) a fluid opening in the tip of the hollow cone of the ampoule holder;
g) an opening means for a monomer liquid container that is arranged in the side of the ampoule holder facing away from the cartridge head;
h) a monomer liquid container that is arranged in the ampoule holder adjacent to the opening means;
i) a closure cylinder as closure means that is axially arranged on the tip of the cone of the dispensing plunger, whereby the closure cylinder has an external diameter that is equal to or larger than the opening of the hollow cone of the ampoule holder and is situated on the same axis as the opening of the ampoule holder;

j) cement powder that is arranged in a first hollow space of the cartridge that is bordered by the cartridge head with the cartridge closure, the internal wall of the cartridge, and the dispensing plunger;

k) a second hollow space that is bordered by the internal wall of the cartridge, the rear side of the dispensing plunger, and the hollow cone of the conveying plunger;

l) a sleeve that is axially shiftable in the ampoule holder and is arranged above the monomer liquid container and can be axially shifted against the monomer liquid container;

m) an external thread on the external side of the ampoule holder;

n) a manually-operated closure head of the ampoule holder that includes an internal thread, whereby the internal thread of the closure head engages the external thread of the ampoule holder, and whereby the closure head rests on the axially shiftable sleeve;

o) an internal thread on an end of the cartridge opposite from the ampoule head that is engaged by the external thread of the ampoule holder; whereby p) an axial motion of the ampoule holder in the direction of the cartridge head causes the closure cylinder to enter into the fluid opening of the hollow cone and to close the fluid opening in gas- and liquid-tight manner and whereby a further motion of the ampoule holder in the direction of the cartridge head reduces the volume of the second hollow space.

The device according to one embodiment can be used advantageously by the user since, having placed the device on a level support, the user only needs to rotate the closure head of the ampoule holder to obtain a ready-mixed bone cement dough after a few seconds that contains no or hardly any air inclusions. The processes of opening the monomer liquid container, monomer transfer, and mixing proceeds in order and automatically simply by repeatedly rotating the closure head of the ampoule holder with the ampoule holder connected to it. Accordingly, the user errors during the opening of the monomer liquid container, the monomer transfer, and the mixing of the monomer liquid with the cement powder known from prior cementing technology are excluded by the design features. This increases the user safety significantly. The device can easily be used by untrained personnel in this context.

A method according to one embodiment can be implemented, for example, with the exemplary device for mixing of the cement powder and the monomer liquid while producing bone cement dough. An exemplary method that is preferred according to one embodiment can be implemented with the following steps proceeding in the order given:

setting up the cartridge on a support with the foot downwards;

rotating the closure head onto the external thread of the ampoule holder;

shifting the sleeve against the monomer liquid container;

moving the monomer liquid container with the opening device;

opening the monomer liquid container;

monomer liquid flowing from the monomer liquid container through the fluid opening of the ampoule holder into the second hollow space;

shifting the ampoule holder in the direction of the cartridge head until the external thread of the ampoule holder engages the internal thread of the cartridge;

rotating the closure head with the ampoule holder connected to it, whereby the external thread of the ampoule holder rotates into the internal thread of the cartridge and the ampoule holder is being moved in the direction of the cartridge head;

supernatant air or other gases over the monomer liquid in the second hollow space exiting through the fluid opening of the hollow cone of the ampoule holder;

closing the fluid opening of the ampoule holder upon further motion of the ampoule holder in the direction of the cartridge head;

extrusion of the monomer liquid from the second hollow space through the feedthrough in the dispensing plunger into the compacted cement powder by shifting the ampoule holder against the dispensing plunger, whereby the hollow cone of the conveying plunger drives against the cone of the dispensing plunger and reduces the volume of the second hollow space until the second hollow space exists no longer or almost no longer;

production of the bone cement dough by swelling of the monomer liquid-wetted cement powder;

shift of the axially mobile stopper in the dispensing opening by the bone cement dough upon further axial motion of the ampoule holder and the dispensing plunger in the direction of the cartridge head;

removal of the cartridge closure and of the foot; and in one embodiment, extrusion of the bone cement dough through further rotating the ampoule holder.

Moreover, a second method is preferred according to one embodiment. Said method for the mixing and dispensing of polymethylmethacrylate bone cement using the exemplary device according to one embodiment is characterized by the following steps proceeding in the order given:

setting up the cartridge on a support with the cartridge head as foot;

rotating the closure head onto the external thread of the ampoule holder;

shifting the sleeve against the monomer liquid container;

moving the monomer liquid container with the opening device;

opening the monomer liquid container;

monomer liquid flowing from the monomer liquid container through the fluid opening of the ampoule holder into the second hollow space;

rotating the closure head with the ampoule holder connected to it, whereby the external thread of the ampoule holder engages the internal thread of the cartridge and the ampoule holder is being moved in the direction of the cartridge head;

supernatant air or gas over the monomer liquid in the second hollow space exiting through the fluid opening of the hollow cone of the ampoule holder;

closing the fluid opening of the ampoule holder upon further motion of the ampoule holder in the direction of the cartridge head;

extrusion of the monomer liquid from the second hollow space through the feedthrough in the dispensing plunger into the compacted cement powder by shifting the ampoule holder against the dispensing plunger, whereby the hollow cone of the ampoule holder drives against the cone of the dispensing plunger and reduces the volume of the second hollow space until the second hollow space exists no longer or almost no longer;

production of the bone cement dough by swelling of the monomer liquid-wetted cement powder;

shift of the axially mobile stopper in the dispensing opening by the bone cement dough upon further axial motion of the ampoule holder and the dispensing plunger in the direction of the cartridge head;

removal of the cartridge closure and of the foot; and in one embodiment, extrusion of the bone cement dough through further rotating the ampoule holder.

A variant of both exemplary methods is characterized by the following steps proceeding in the order given such that, when the mobile stopper is shifted, a coloured ring connected to the mobile stopper moves in front of a transparent window of the foot as a marker means and thus indicates to the medical user that the mixing of the cement powder with the monomer liquid has taken place.

Figure 2:
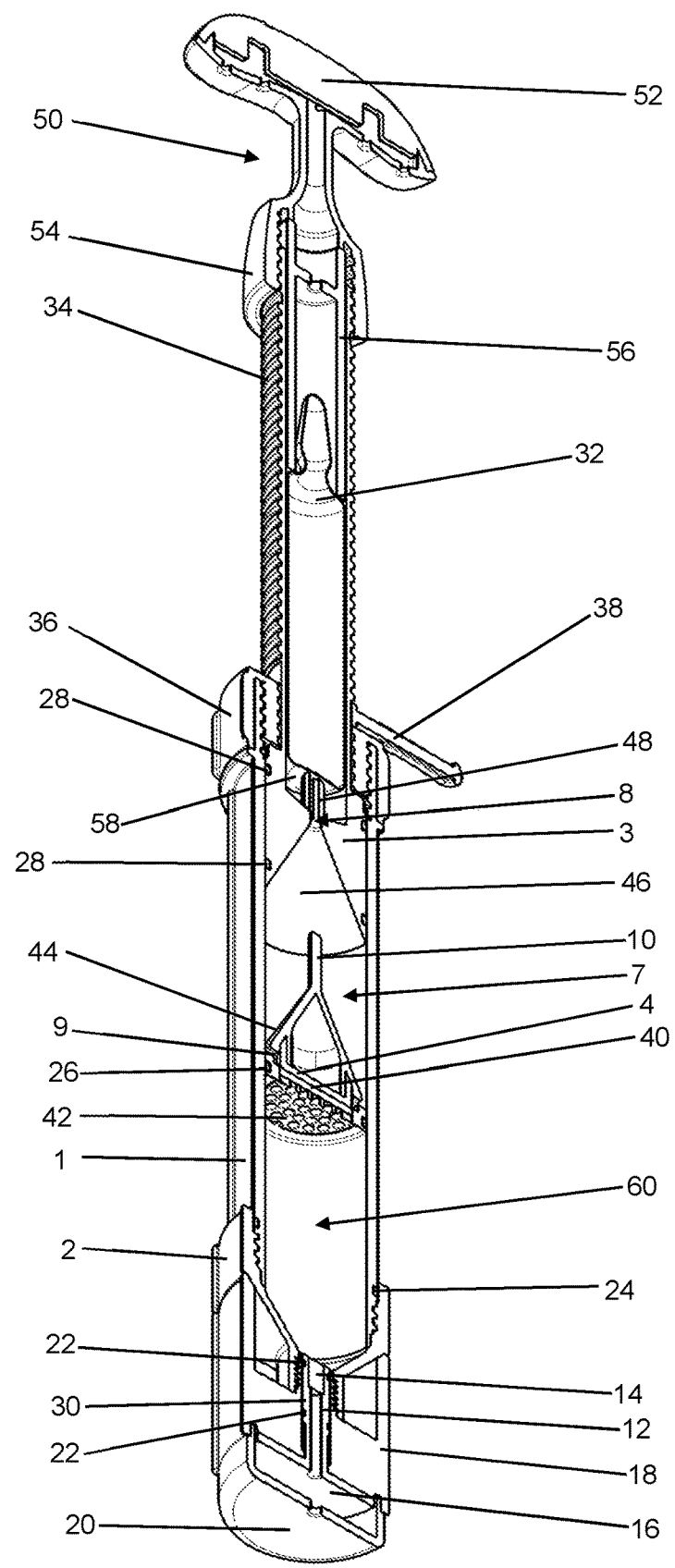
FIG. 2: illustrates a schematic perspective cross-sectional view of the device according to FIG. 1 without the monomer liquid and the cement powder.
Figure 3:
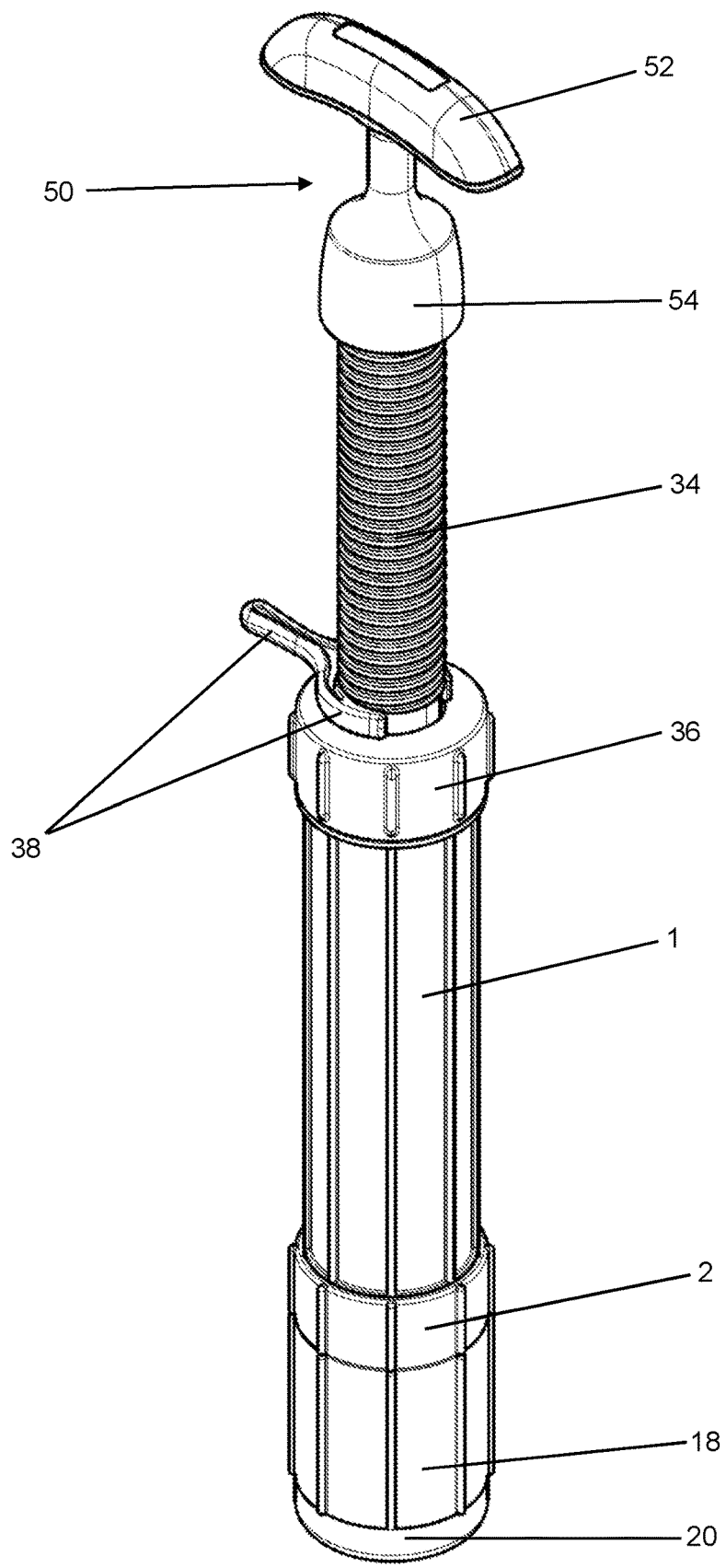
FIG. 3: illustrates a schematic perspective external view of the device according to FIGS. 1 and 2.
Figure 8:
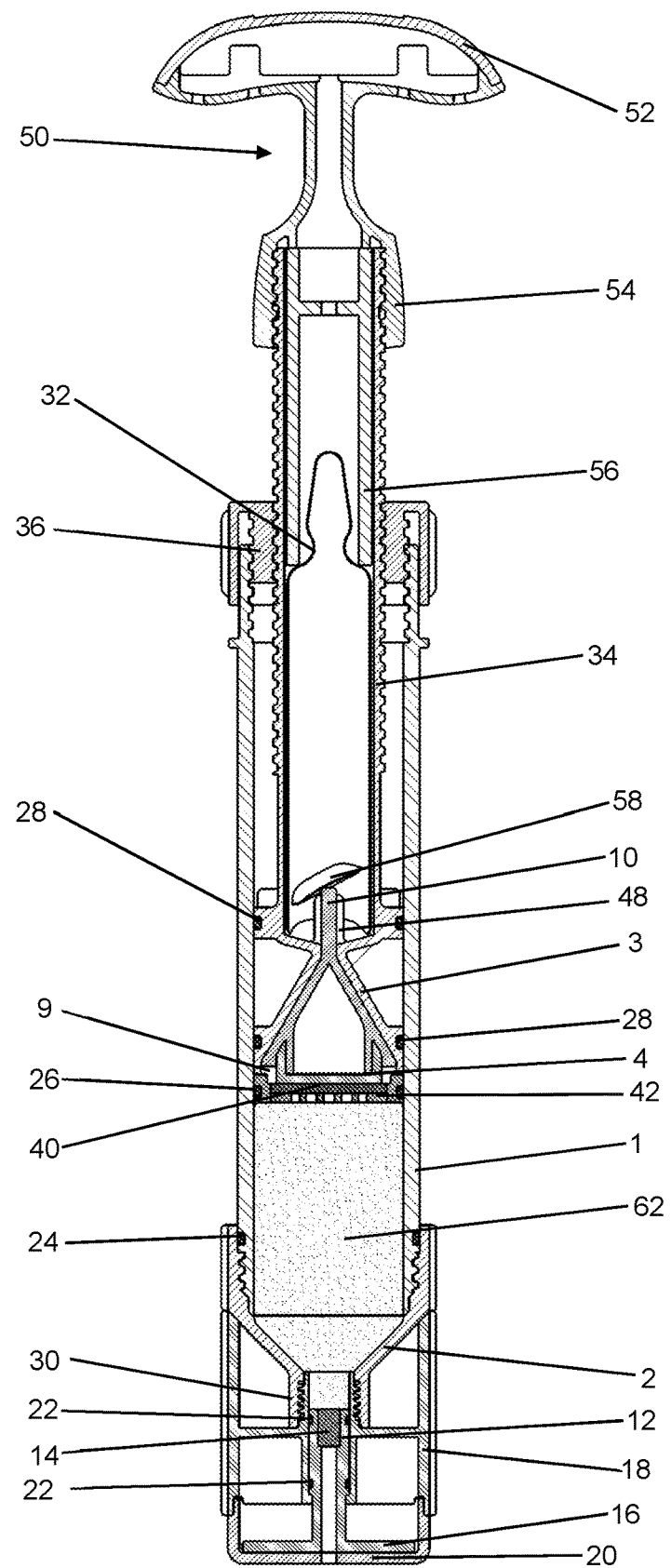
FIG. 8: illustrates a schematic cross-sectional view of the device according to FIGS. 1 to 7 with the stopper pushed forward and marker means as an indicator of the bone cement dough being ready for use.
Figure 9:
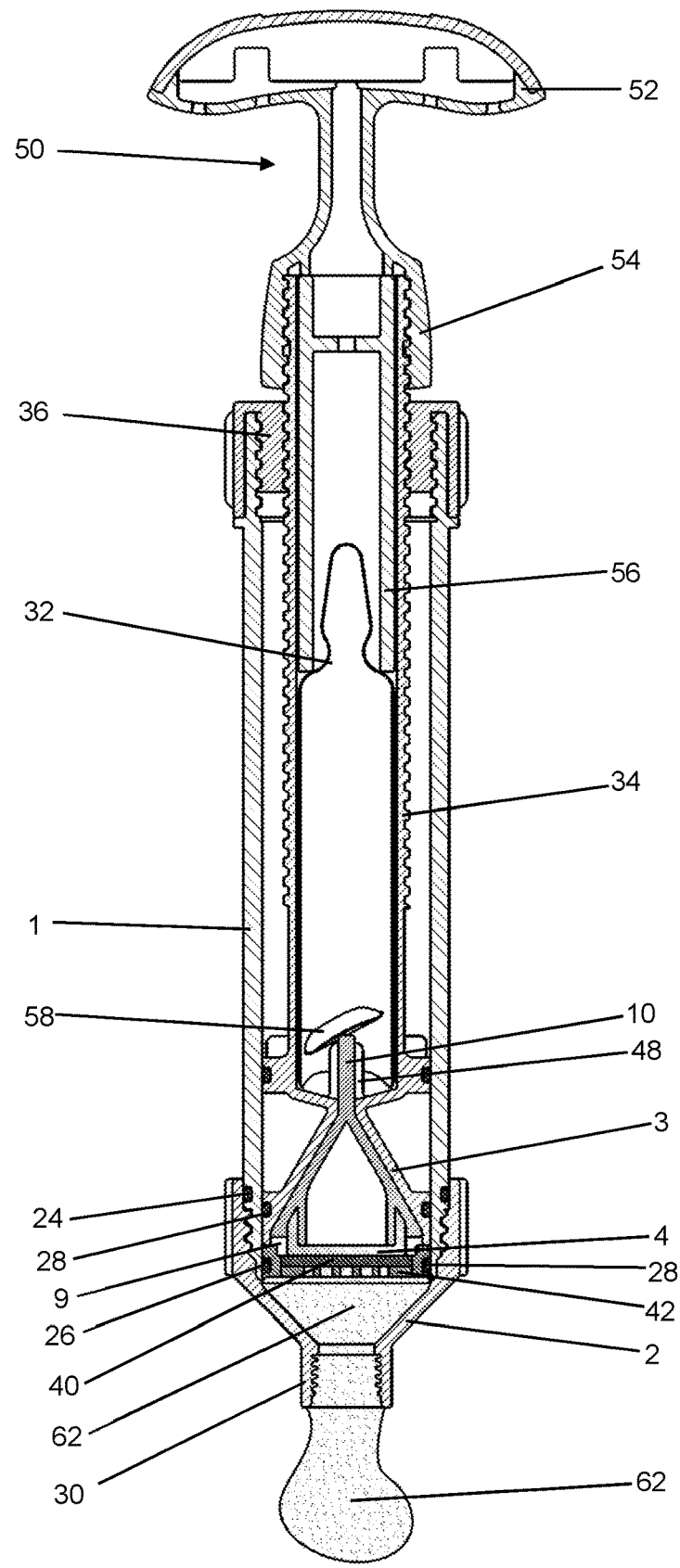
FIG. 9: illustrates a schematic cross-sectional view of the device according to FIGS. 1 to 8 during the dispensation of the bone cement dough.
Figure 10:
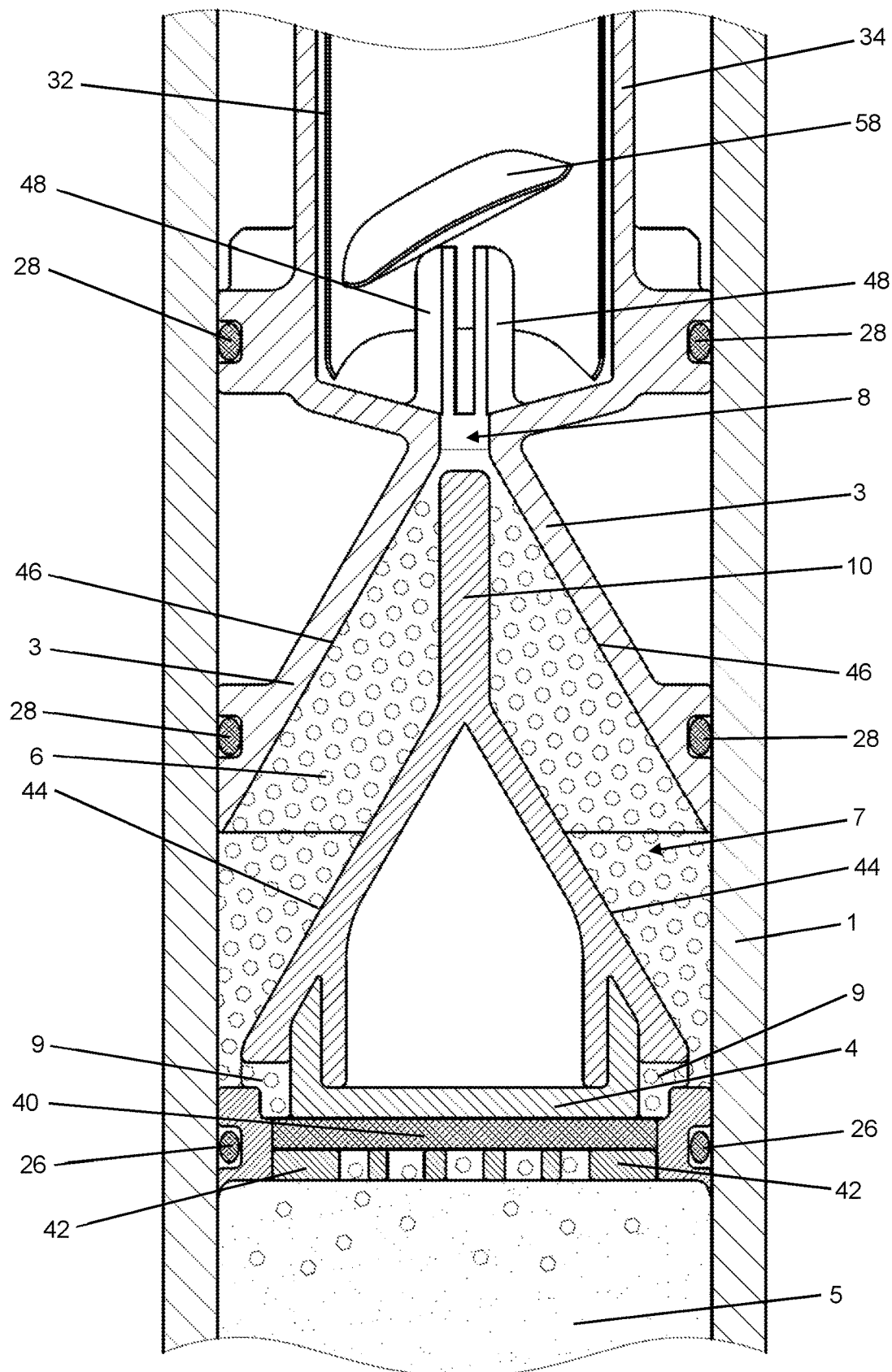
FIG. 10: illustrates a schematic cross-sectional view of a detail magnification of the device according to FIGS. 1 to 9 shortly before the fluid opening is being closed.

FIGS. 1 to 10 illustrate depictions of a first device according to one embodiment. FIGS. 1 to 9 illustrate various schematic total views of the exemplary first device according to one embodiment. FIG. 10 illustrates schematic cross-sectional views as detail views in the form of detail magnifications through a region of the device according to one embodiment. In this context, FIGS. 1 to 3 illustrate the first device according to one embodiment in a starting state, whereas FIGS. 4 to 10 illustrate cross-sectional views of the first device according to one embodiment during the use of the device in order to illustrate an exemplary method according to one embodiment.

In one embodiment, the device has a tube-shaped cartridge 1 made of a plastic material with a cylindrical internal space. The cartridge 1 can be closed on its front side by a funnel-shaped cartridge head 2 made of plastics. The front side of the cartridge 1 is on the bottom in FIGS. 1 to 9. The tip of the funnel-shaped cartridge head 2 can have a central dispensing opening arranged on it, which can initially be closed in the starting state. According to an alternative embodiment, the cartridge head 2 can just as well be a flat cap or have a different shape. It is basically feasible just as well to provide the cartridge head 2 and the cartridge 1 as a single part. However, in order to simplify the assembly of the device, it is preferred that the cartridge head 2 is connected to the cartridge 1 in the form of a separate part, for example is screwed or plugged onto it.

In one embodiment, a rear side of the cartridge 1 opposite from the front side of the cartridge 1 can have a conveying plunger 3 arranged in the internal space of the cartridge 1 that is supported in the internal space of the cartridge 1 such as to be axially mobile in the direction of the front side of the cartridge 1. A dispensing plunger 4 can be arranged between the conveying plunger 3 and the front side of the cartridge 1. The conveying plunger 3 and the dispensing plunger 4 can be manufactured from plastics, at least in part. A first hollow space 60 is formed on the inside of the device (see FIG. 2) between the dispensing plunger 4 and the front side of the cartridge 1 and/or the cartridge head 2. The first hollow space 60 can contain a cement powder 5 as one of the starting components of the bone cement dough 62 to be produced (see FIGS. 7 to 9). In one embodiment, the cement powder 5 is pressed in or at least stored in compact form in the cartridge head 2 between the dispensing plunger 4 and the cartridge head 2 and in the internal space of the cartridge 1 in the first hollow space 60 in order to simplify the introduction and distribution of a monomer liquid 6 in the cement powder 5 through the use of capillary forces between the cement powder particles.

The dispensing plunger 4 and the conveying plunger 3 and the internal walls of the cartridge 1 can border a second hollow space 7 in the internal space of the cartridge 1. A fluid opening 8 through which the monomer liquid 6 is conveyable into the second hollow space 7 can be arranged on the tip of the funnel-shaped conveying plunger 3. The fluid opening 8 can be implemented as a through-going cylindrical bore hole through the conveying plunger 3. The dispensing plunger 4 can have a feedthrough 9 provided in it that commences on the external circumference of the dispensing plunger 4 and through which the monomer liquid 6 can flow or be conducted from the second hollow space 7 to the cement powder 5 in the first hollow space 60 (see FIG. 6).

The dispensing plunger 4 can include, on its rear side, a cone-shaped surface 44 that corresponds to a negative form with respect to a funnel-shaped surface 46 in the funnel-shaped conveying plunger 3. In this context, one embodiment can provide the dispensing plunger 4 to be able to touch by its cone-shaped surface 44 against the funnel-shaped surface 46 of the conveying plunger 3 by matching surfaces, when the conveying plunger 3 is pushed against the dispensing plunger 4 (see FIGS. 7 to 9). In this context, the volume of the second hollow space 7 can be reduced to zero such that the second hollow space 7 is disappeared in this state.

One embodiment can provide a closure means 10 in the form of a cylindrical pin to be arranged on the tip of the cone-shaped surface 44 on the rear side of the dispensing plunger 4. In this context, the external circumference of the closure means 10 can match the internal wall of the fluid opening 8 such that the fluid opening 8 is closable by the closure means 10 in gas-tight and fluid-tight manner. For this purpose, the external circumference of the closure means 10 can be equal to or somewhat larger than the internal circumference of the fluid opening 8. The closure means 10 can be appropriately elongated in this context such that it closes the fluid opening 8 once the distance between the dispensing plunger 4 and the conveying plunger 3 is less than a minimum distance. In this context, the closure means 10 can in one embodiment be pushed through the fluid opening 8 when the conveying plunger 3 is pushed in the direction of the dispensing plunger 4. Particularly in one embodiment, the closure means 10 can close the fluid opening 8 in any position of the conveying plunger 3 relative to the dispensing plunger 4 once the distance between the dispensing plunger 4 and the conveying plunger 3 is less than a minimum distance.

In one embodiment, the fluid opening 8 and the closure means 10 can be arranged along or parallel to the cylinder axis of the cylindrical internal space of the cartridge 1 or be aligned with each other.

To an informed expert it is clear in this context that this embodiment with a central fluid opening 8 in the conveying plunger 4 can easily be applied to a non-central fluid opening as well. Likewise, a closure means that is not arranged on the cylinder axis of the internal space of the cartridge 1 can be implemented. Moreover, multiple fluid openings can easily be provided for conducting the monomer liquid 6 through the conveying plunger 3. Likewise, multiple closure means can easily be arranged on the rear side of the dispensing plunger 4. It is an important and central aspect for the implementation of one embodiment that all fluid openings that may be present are closable by the closure means that may be present before the conveying plunger 3 and the dispensing plunger 4 touch against each other and before the volume of the second hollow space 7 is reduced to zero, whereby all fluid openings that may be present remain closed by the closure means that may be present, when the conveying plunger 3 is driven further in the direction of the dispensing plunger 4. Based on this aspect, a person skilled in the art can easily find closure means for the fluid openings that are similar or equal in effect and shall be considered to be included in the scope of the present embodiment.

The dispensing opening in the cartridge head 2 can initially be closed by a stopper 12 (see FIGS. 1 to 8). The stopper 12 can have a passage arranged in it through which gases can be evacuated from and conducted into the first hollow space 60. In order to prevent cement powder 5 from leaking, one embodiment can provide a pore filter 14 that is impermeable to the cement powder 5, but is permeable to gases, to be arranged in the passage. A coloured marker means 16 can be provided on the stopper 12 in the form of a coloured ring disk that allows a motion of the stopper 12 against the dispensing opening to be recognised visually. For this purpose, the coloured marker means 16 can for example be red or of any other signal colour. However, other (including non-visual) methods are conceivable that indicate a motion of the stopper 12 against the dispensing opening to the user.

A foot 18 with a lower foot part 20 can be arranged on the cartridge head 2. The stopper 12 can in one embodiment be mobile with respect to the foot 18. The lower part of the foot 20 can in one embodiment be transparent to allow the position of the marker means 16 to be recognised.

Particularly in one embodiment, the marker means 18 can initially be hidden in a non-transparent part of the foot 18 and is moved into the transparent lower part of the foot 20 only when the stopper 12 is moved out of the dispensing opening, in which place it is then visible through the transparent lower foot part 20.

In order to prevent leakage of monomer liquid 6 and bone cement dough 62 and/or to seal the first hollow space 60 from the second hollow space 7 or other areas from each other, seals can be provided. Accordingly, two sealing rings 22 can be arranged in two circumferential grooves on an external circumference of the stopper 12 to seal the stopper 12 with respect to the dispensing opening and/or with respect to the foot 18. A sealing ring 24 can be provided to be arranged in a circumferential groove on the external side of the cartridge 1 and to seal the cartridge head 2 with respect to the cartridge 1. A sealing ring 26 can be arranged in a circumferential groove on the external circumference of the dispensing plunger 4 to seal the dispensing plunger 4 with respect to the internal wall of the cartridge 1. Two sealing rings 28 can be arranged in two circumferential grooves on the external circumference of the conveying plunger 3 and on the external circumference of a container 34 that can be arranged on the rear side of the conveying plunger 3 to seal the conveying plunger 3 and the container 34 with respect to the internal wall of the cartridge 1.

A socket 30 that surrounds the dispensing opening can be provided on the tip of the cartridge head 2. The socket 30 can have an internal thread provided in it, into which a dispensing tube (not illustrated) with a matching external thread can be screwed. The foot 18 can be detachably attached to the socket 30 in the same internal thread or on a different attachment means of the socket 30 by means of a matching external thread or a different matching counter attachment means.

In order to obtain a complete full-prepacked mixing system, a monomer liquid container 32, for example in the form of an ampoule made of glass or plastics that can be fractured, can be arranged in the container 34, which can be arranged on the rear side of the conveying plunger 3 for this purpose. The monomer liquid container 32 can contain the monomer liquid 6. The internal space of the container 34 can be connected in fluid-permeable manner to the second hollow space 7 via the fluid opening 8. By this means, a monomer liquid 6 released in the container 34 can flow from the container 34 into the second hollow space 7, when the device is held or set up with the cartridge head 2 downwards.

A ring sleeve 36 with an internal thread can be attached to a rear-side end of the cartridge 1 that is opposite from the cartridge head 2. This simplifies the assembly of the device provided it is present as a part that is separate from cartridge 1. For this purpose, the ring sleeve 36 can be screwed into an internal thread on the rear-side end of the cartridge 1 by means of a matching external thread.

According to a preferred development, one embodiment can provide the container 34 to include an external thread on its external circumference. Particularly in one embodiment, said external thread matches the internal thread of the ring sleeve 36 or an internal thread on the rear-side end of the cartridge 1. By this means, the container 34 can be screwed into the cartridge 1. This can enable a propulsion of the conveying plunger 3 in the internal space of the cartridge 1. Theoretically, as an alternative to the container 34, a cylinder (not illustrated) with a matching external thread can be attached to or loosely arranged on the rear side of the conveying plunger 3 such that the conveying plunger 3 and, by means of the conveying plunger 3, the dispensing plunger 4 as well is pushable inside the internal space of the cartridge 1 in the direction of the cartridge head 2 by the cylinder being screwed in.

In order to prevent the container 34 and/or the ring sleeve 36 from moving prematurely or inadvertently against the cartridge 1, a locking means 38 that can be pulled off can be provided. For this purpose, the locking means 38 can be shaped like a brace that engages on the external circumference of the container 34 or a different rear-side extension of the conveying plunger 3 and rests on the rear-side end of the cartridge 1 or on the ring sleeve 36.

One embodiment can provide a pore filter 40 to be arranged in or on the dispensing plunger 4. The feedthroughs 9 can be covered by the pore filter 40. This prevents cement powder 5 from the first hollow space 60 from penetrating into the feedthroughs 9 or into the second hollow space 7, where it would form a gel-like barrier upon reaction with the monomer liquid 6 and thus counteract a distribution of the monomer liquid 6 in the cement powder 5.

The pore filter 40 can in one embodiment be a circular disk. The pore filter 40 can be covered by a disk 42 and can be attached in the dispensing plunger 4. To enable and/or facilitate the monomer liquid 6 being conducted through and distributed in the first hollow space 60 and in the cement powder 5, a multitude of boreholes or holes can be provided in the disk 42 (see FIG. 2).

Multiple pins 48 can be arranged in the internal space of the container 34. Said pins 48 can touch against a cartridge base 58 of the monomer liquid container 32. The pins 48 can be used to fracture the monomer liquid container 32 at the cartridge base 58 or to puncture or cut the monomer liquid container 32 such as to open it. In one embodiment, the pins 48 can be arranged around the merging site of the fluid opening 8. The pins 48 can be situated at an appropriate distance from each other such that they do not cover an extension of the fluid opening 8 in order to enable the closure means 10 to pass through.

An opening means 50 for opening the monomer liquid container 32 can be arranged on the rear side of the container 34 that faces away from the conveying plunger 3. The opening means 50 can include a manually operated handle 52 and a cap 54 for this purpose. One embodiment can provide the cap 54 to be supported against the container 34 such as to be mobile, whereby the cap 54 can in one embodiment be screwed onto the external thread of the container 34. The container 34 can be open on its rear side. On the inside of the container 34, a sleeve 56 in the form of a piece of tube can be supported against the container 34 such as to be mobile as part of the opening means 50. The monomer liquid container 32 is openable inside the container 34 through a motion of the sleeve 56 into the container 34. In one embodiment, an ampoule as monomer liquid container 32 is pushed appropriately onto the pins 48 by the cartridge base 58 such that the cartridge base 58 fractures or breaks off and the ampoule is thus opened (see FIG. 4). By this means, the monomer liquid 6 can be released from the monomer liquid container 32 on the inside of the container 34.

The work-flow of a method according to one embodiment is illustrated in the following based on FIGS. 1 to 10 using the device according to one embodiment for an example.

The device is initially in the original state or storage state illustrated in FIGS. 1 to 3. In this state, the device can be evacuated through suitable openings and can be sterilised with ethylene oxide.

Figure 4:
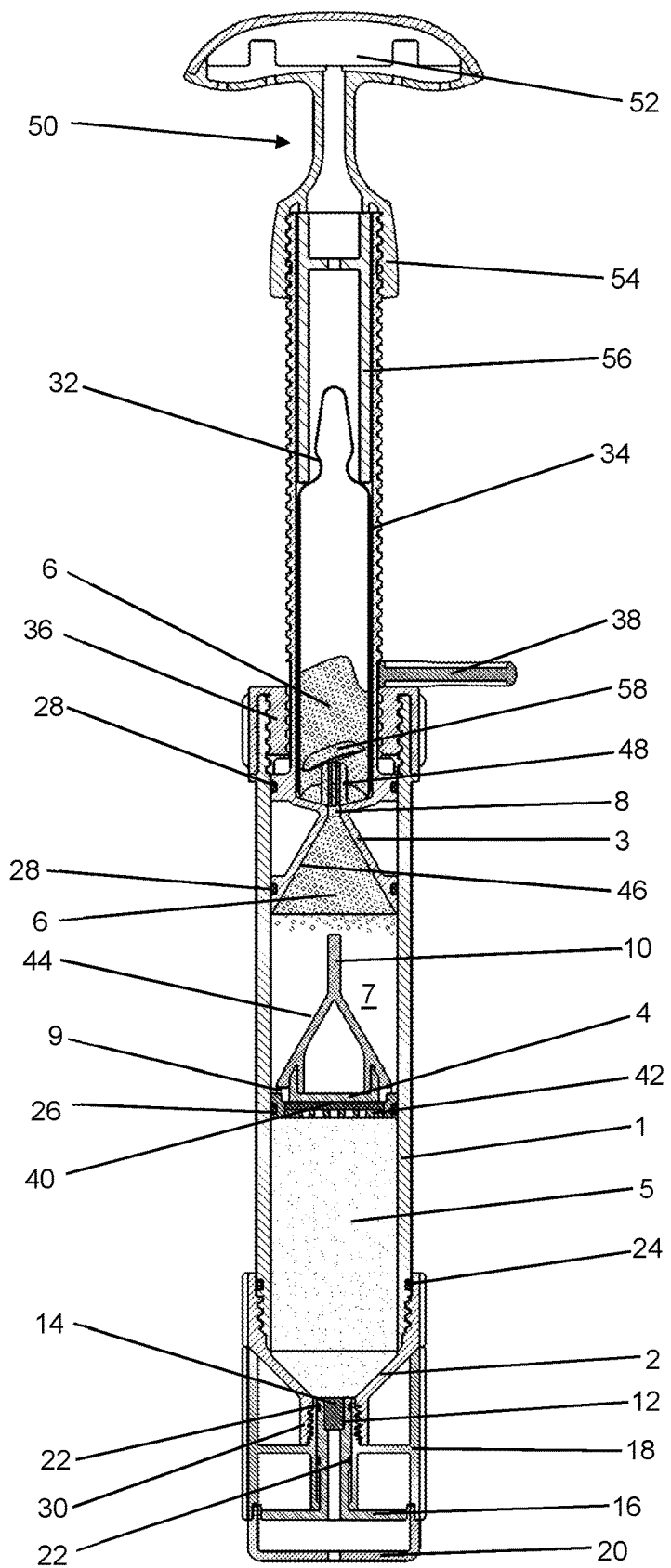
FIG. 4: illustrates a schematic cross-sectional view of the device according to FIGS. 1 to 3 with an opened monomer liquid container in it.

Subsequently, the foot 18 of the device can be placed on a level support. Then the opening means 50 can be screwed onto the container 34, until the cartridge base 58 of the monomer liquid container 32 fractures. Due to the monomer liquid container 32 fracturing, the monomer liquid 6 contained therein is released and can flow from the container 34 through the fluid opening 8 into the second hollow space 7. This situation is illustrated in FIG. 4.

Figure 5:
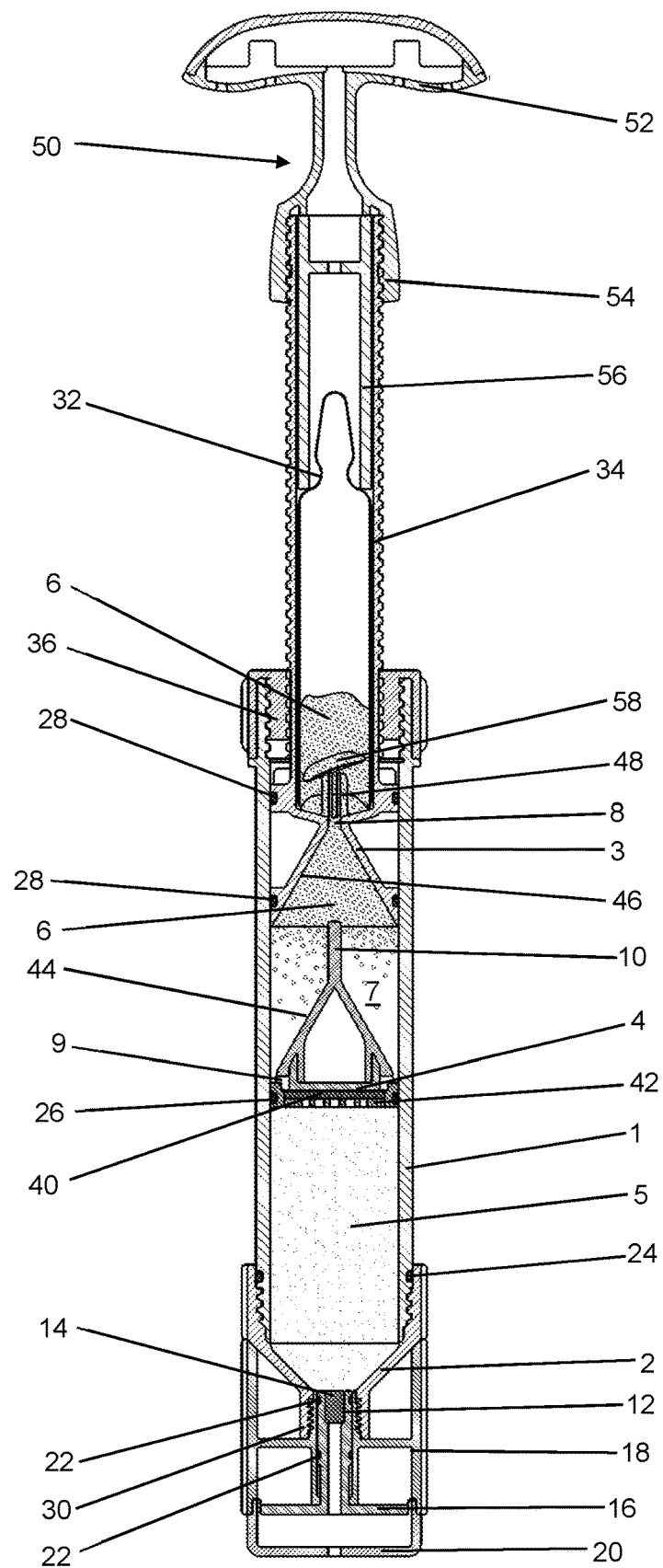
FIG. 5: illustrates a schematic cross-sectional view of the device according to FIGS. 1 to 4 with a locking element pulled off.

Subsequently, the locking means 38 can be pulled off. The container 34 can now the inserted more deeply into the cartridge 1, until the external thread on the container 34 encounters the internal thread on the ring sleeve 36 and blocks the container 34 from moving further into the cartridge 1. This situation is illustrated in FIG. 5. Along with the container 34, the conveying plunger 3 can also be pushed in the direction of the dispensing plunger 4 in the internal space of the cartridge 1. In this context, one embodiment can provide that the closure means cannot yet close the fluid opening 8 in the state illustrated in FIG. 5 in order to enable a continued flow of the monomer liquid 6 through the fluid opening 8 into the second hollow space 7. For this purpose, the closure means 10 originating from the rear side of the dispensing plunger 4 can simply be designed to not be long enough. And yet the volume of the second hollow space 7 can be reduced through the motion of the conveying plunger 3 in the direction of the dispensing plunger 4.

Figure 6:
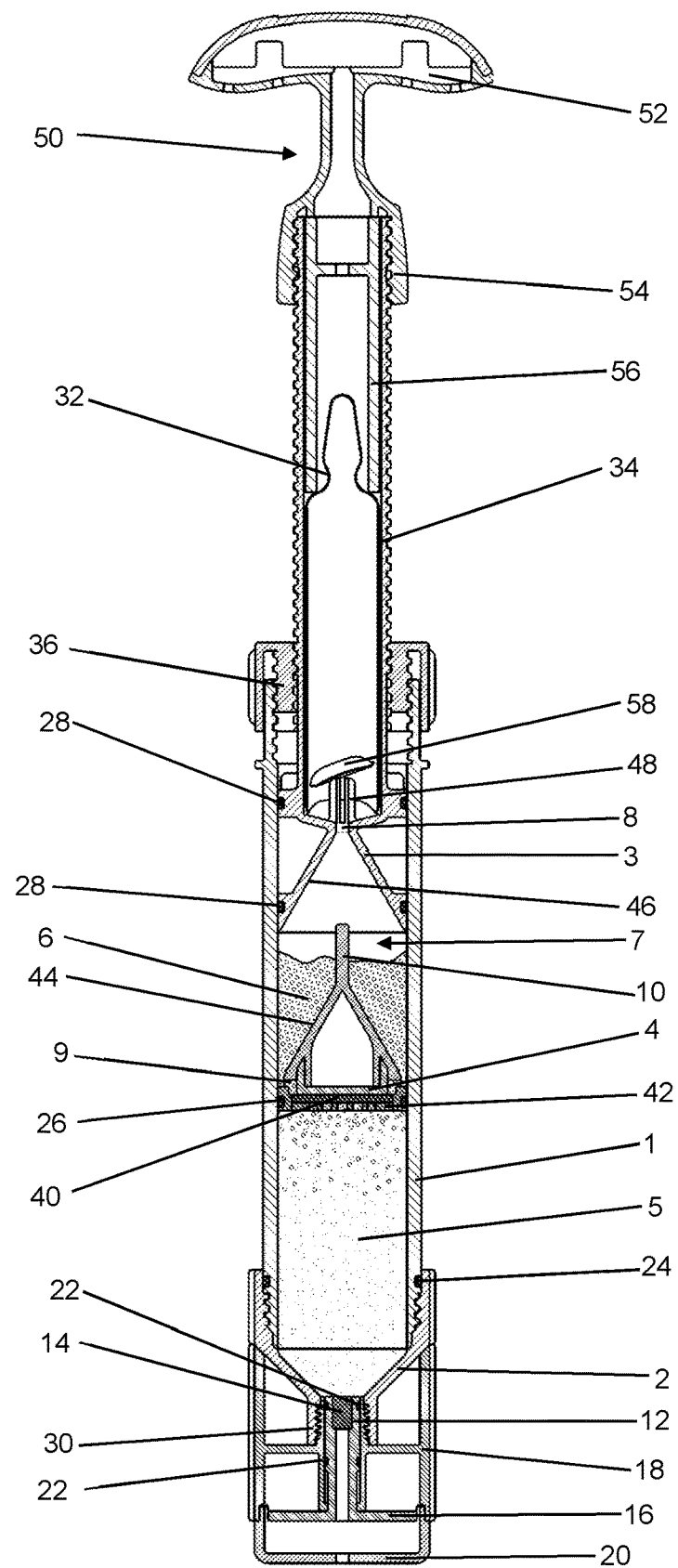
FIG. 6: illustrates a schematic cross-sectional view of the device according to FIGS. 1 to 5, in which the external thread of the container engages the internal thread of the ring sleeve that is connected to the cartridge.

The ring sleeve 36 can now be screwed upwards, away from the cartridge head 10 of the cartridge 1, until the internal thread of the ring sleeve 36 engages the external thread of the container 34. Meanwhile, the monomer liquid 6 has flown completely from the container 34 into the second hollow space 7 and can already begin to flow through the feedthrough 9 in the dispensing plunger 4 and, if applicable, through the pore disk 40 and the disk 42 into the second hollow space 60. This situation is illustrated in FIG. 6.

Once the monomer liquid 6 flows into the first hollow space 60, it becomes distributed between the powder particles of the cement powder 5 and thus in the cement powder 5 due to capillary forces. Then, the container 34 can be screwed more deeply into the cartridge 1 by rotating the container 34 against the ring sleeve 36 and/or against the cartridge 1. The conveying plunger 3 is pushable progressively further in the direction of the dispensing plunger 4 in this context. Once a minimum distance between the conveying plunger 3 and the dispensing plunger 4 is reached, the conveying plunger 3 continuing to move towards the dispensing plunger 4 allows the closure means 10 to penetrate into the fluid opening 8 and close the fluid opening 8 in liquid-tight and gas-tight manner. One embodiment can provide that for no gas inclusions and/or air inclusions to be present in the second hollow space 7 at this point in time, because these were all able to escape upwards out of the fluid opening 8 by this time (see FIG. 10). This can be effected by the funnel-shaped surface 46 if the slope is sufficiently large. In one embodiment, the fluid opening 8 can remain closed when the conveying plunger 3 is moved further towards the dispensing plunger 4.

Figure 7:
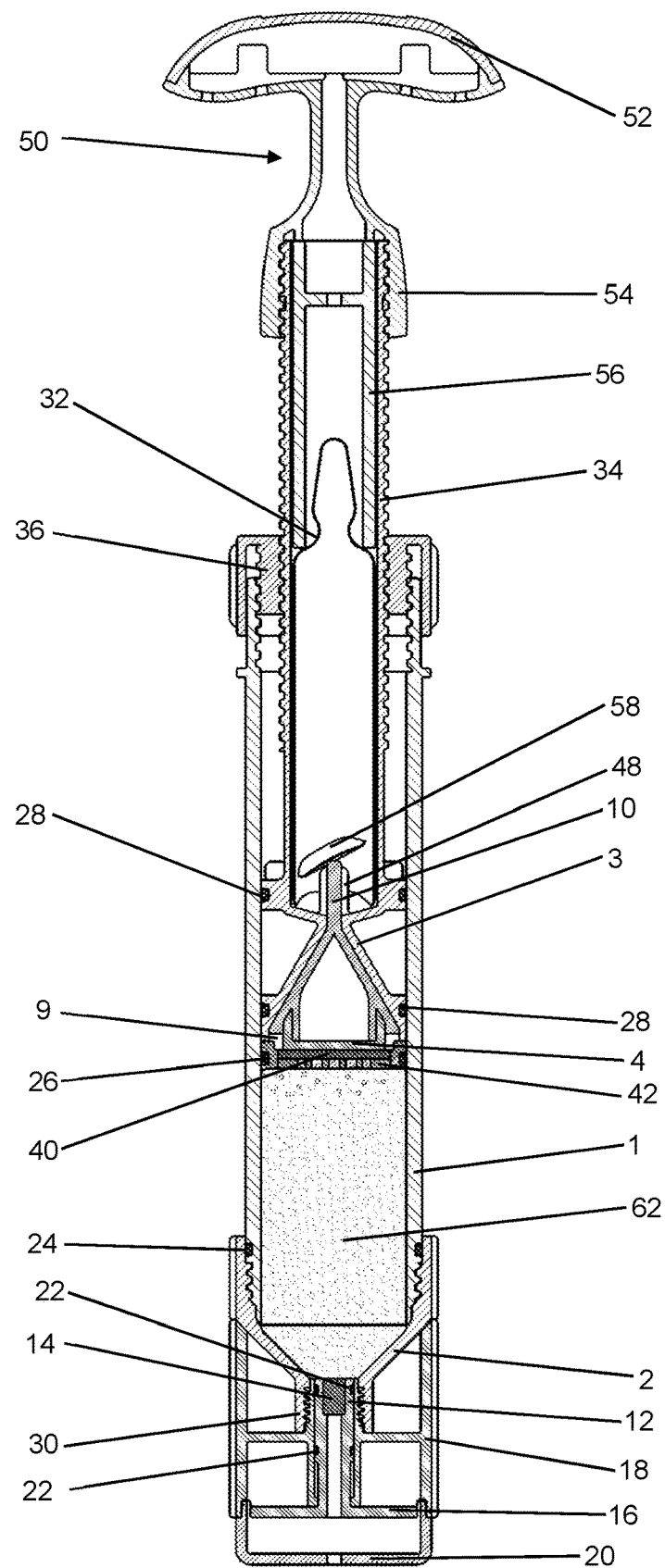
FIG. 7: illustrates a schematic cross-sectional view of the device according to FIGS. 1 to 6 after the monomer liquid has been pressed into the cement powder.

The container 34 can now be screwed even more deeply into the cartridge 1. The monomer liquid 6 is pressed from the second hollow space 7 into the cement powder 5 in the first hollow space 60 and becomes distributed therein in this context. Lastly, the conveying plunger 3 can encounter the dispensing plunger 4 such that the funnel-shaped surface 46 of the conveying plunger 3 touches against the matching cone-shaped surface 44 on the rear side of the dispensing plunger 4, in one embodiment touching against it with matching surfaces. In the meantime, the cement powder 5 exposed to the monomer liquid 6 swells and produces the bone cement dough 62. This situation is illustrated in FIG. 7.

The container 32 can be screwed even more deeply into the cartridge 1, when the bone cement 62 is produced up to the dispensing opening and/or when the cement powder 5 is wetted by the monomer liquid 6 all the way up to the dispensing opening, since only then a flowable material is obtained in the first hollow space 60 that is pushable into the dispensing opening. The stopper 12 can be moved in the dispensing opening through the motion of the bone cement dough 62. This can be recognised visually through a shift of the marker means 16 into the transparent part of the foot 20 such that the user is aware that the bone cement dough 62 is now ready for use. This situation is illustrated in FIG. 8.

Next, the foot 18 with the stopper 12 can be detached from the dispensing opening. Subsequently, the bone cement dough 62 can be dispensed from the dispensing opening by screwing the container 34 further in and thus by further propelling the conveying plunger 3 and the dispensing plunger 4 in the direction of the dispensing opening. This situation is illustrated in FIG. 9. One embodiment can provide for the user to connect a dispensing tube (not illustrated) to a socket 30 or to a different site for application of the bone cement dough 62.

Figure 11:
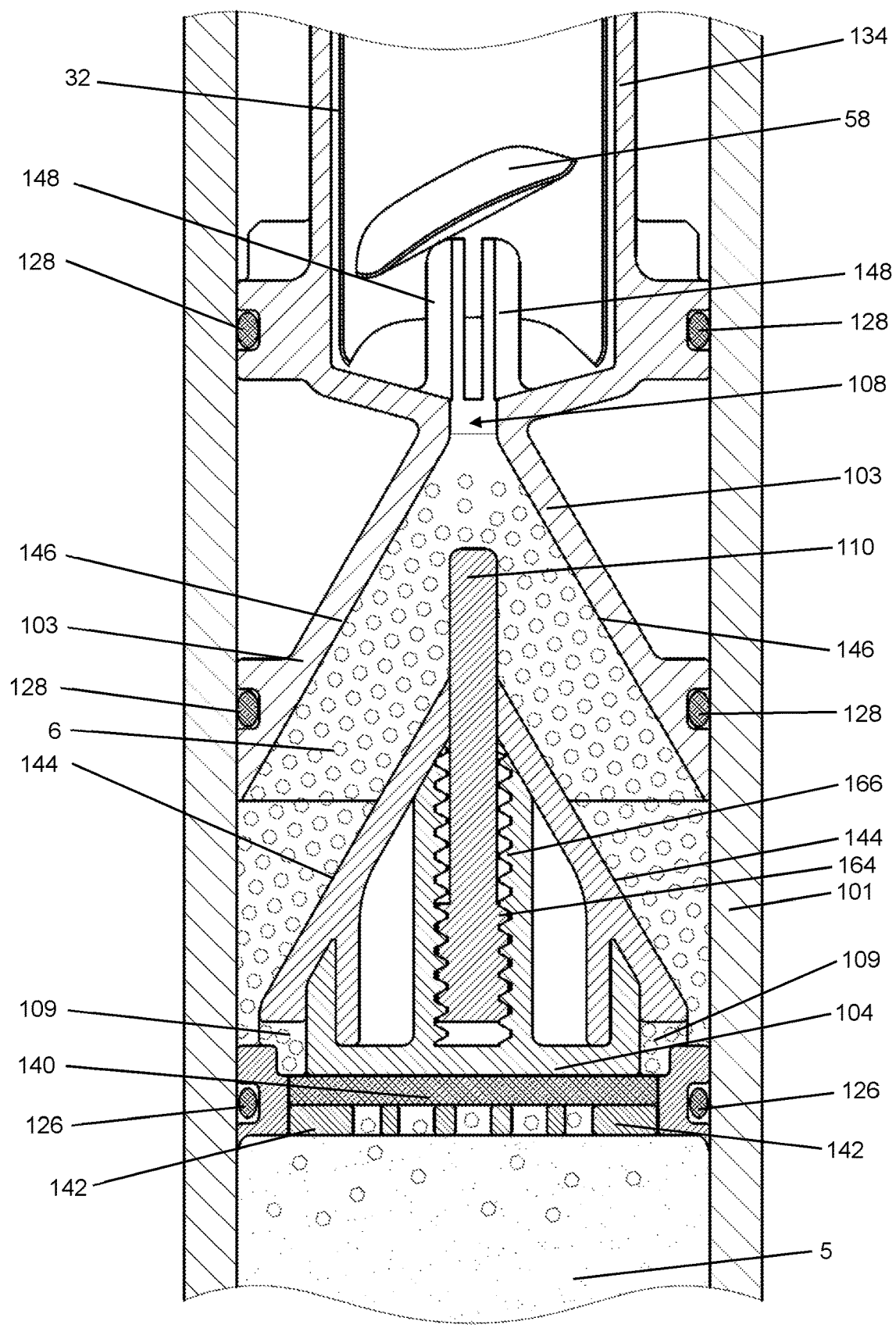
FIG. 11: illustrates a schematic cross-sectional view of a detail magnification of an alternative second device according to one embodiment with a closure means that can be set variably.

FIG. 11 illustrates a schematic cross-sectional view of a detail magnification of an alternative device according to one embodiment with a closure means 110 that can be set variably. The detail illustrated in FIG. 11 corresponds to the detail illustrated in FIG. 10 in order to illustrate the difference between the two embodiments. The second exemplary embodiment according to FIG. 11 corresponds to the first exemplary embodiment according to FIGS. 1 to 10 except for the capability to set the closure means 110 variably.

In a second exemplary embodiment, the device has a tube-shaped cartridge 101 made of a plastic material with a cylindrical internal space. The cartridge 101 can be closed on its front side by a funnel-shaped cartridge head (not illustrated) made of plastics. The front side of the cartridge 101 is on the bottom in FIG. 11. The tip of the funnel-shaped cartridge head can have a central dispensing opening arranged on it, which can initially be closed in the starting state. According to an alternative embodiment, the cartridge head can just as well be a flat cap or have a different shape.

In one embodiment, a rear side in the internal space of the cartridge 101 opposite from the front side of the cartridge 101 can have a conveying plunger 103 arranged on it that is supported in the internal space of the cartridge 101 such as to be axially mobile in the direction of the front side of the cartridge 101. A dispensing plunger 104 can be arranged between the conveying plunger 103 and the front side of the cartridge 101. The conveying plunger 103 and the dispensing plunger 104 can be manufactured from plastics, at least in part. A first hollow space is formed on the inside of the device between the dispensing plunger 104 and the front side of the cartridge 101 and/or the cartridge head. The first hollow space can contain a cement powder 5 as one of the starting components of the bone cement dough to be produced. In one embodiment, the cement powder 5 is pressed in or at least stored in compact form in the cartridge head between the dispensing plunger 104 and the cartridge head and in the internal space of the cartridge 101 in the first hollow space 60 in order to simplify the introduction and distribution of a monomer liquid 6 in the cement powder 5 through the utilisation of capillary forces between the cement powder particles.

The dispensing plunger 104 and the conveying plunger 103 and the internal walls of the cartridge 101 can border a second hollow space 107 in the internal space of the cartridge 101. A fluid opening 108 through which the monomer liquid 106 is conveyable into the second hollow space 107 can be arranged on the tip of the funnel-shaped conveying plunger 103. The fluid opening 108 can be implemented as a through-going cylindrical bore hole through the conveying plunger 103. The dispensing plunger 104 can have a feed-through 109 provided in it that commences on the external circumference of the dispensing plunger 104 and through which the monomer liquid 6 can flow or be conducted from the second hollow space 107 to the cement powder 5 in the first hollow space.

The dispensing plunger 104 can include, on its rear side, a cone-shaped surface 144 that corresponds to a negative form with respect to a funnel-shaped surface 146 in the funnel-shaped conveying plunger 103. In this context, one embodiment can provide the dispensing plunger 104 to be able to touch by its cone-shaped surface 144 against the funnel-shaped surface 146 of the conveying plunger 103 by matching surfaces, when the conveying plunger 103 is pushed against the dispensing plunger 104. In this context, the volume of the second hollow space 107 can be reduced to zero such that the second hollow space 107 is disappeared in this state.

One embodiment can provide the closure means 110 in the form of a cylindrical pin to be arranged on the tip of the cone-shaped surface 144 on the rear side of the dispensing plunger 104. In this context, the external circumference of the closure means 110 can match the internal wall of the fluid opening 108 such that the fluid opening 108 is closable by the closure means 110 in gas-tight and fluid-tight manner. For this purpose, the external circumference of the closure means 110 can be equal to or somewhat larger than the internal circumference of the fluid opening 108. The closure means 110 can be appropriately elongated in this context such that it closes the fluid opening 108 once the distance between the dispensing plunger 104 and the conveying plunger 103 is less than a minimum distance. In this context, the closure means 110 can in one embodiment be pushed through the fluid opening 108 when the conveying plunger 103 is pushed in the direction of the dispensing plunger 104. Particularly in one embodiment, the closure means 110 can close the fluid opening 108 in any position of the conveying plunger 103 relative to the dispensing plunger 104 once the distance between the dispensing plunger 104 and the conveying plunger 103 is less than a minimum distance.

In one embodiment, the fluid opening 108 and the closure means 110 can be arranged along or parallel to the cylinder axis of the cylindrical internal space of the cartridge 101 or be aligned with each other.

To an informed expert it is clear in this context that this embodiment with a central fluid opening 108 in the conveying plunger 104 can be applied to a non-central fluid opening as well without any difficulty. Likewise, a closure means that is not arranged on the cylinder axis of the internal space of the cartridge 101 can be implemented. Moreover, multiple fluid openings can be provided for conducting the monomer liquid 6 through the conveying plunger 103 without any difficulty. Likewise, multiple closure means can be arranged on the rear side of the dispensing plunger 104 without any difficulty. It is an important and central aspect for the implementation of one embodiment that all fluid openings that may be present are closable by the closure means that may be present before the conveying plunger 103 and the dispensing plunger 104 touch against each other and before the volume of the second hollow space 107 is reduced to zero, whereby all fluid openings that may be present remain closed by the closure means that may be present, when the conveying plunger 103 is driven further in the direction of the dispensing plunger 104. Based on this aspect, a person skilled in the art can easily find closure means for the fluid openings that are similar or equal in effect and shall be considered to be included in the scope of the present embodiment.

The dispensing opening in the cartridge head can initially be closed by a stopper (not illustrated). In order to prevent leakage of monomer liquid 6 and bone cement dough and/or to seal the first hollow space from the second hollow space 107 or other areas from each other, seals can be provided. For this purpose, a sealing ring 126 can be arranged in a circumferential groove on the external circumference of the dispensing plunger 104 to seal the dispensing plunger 104 with respect to the internal wall of the cartridge 101. Two sealing rings 128 can be arranged in two circumferential grooves on the external circumference of the conveying plunger 103 and on the external circumference of a container 134 that can be arranged on the rear side of the conveying plunger 103 to seal the conveying plunger 103 and the container 134 with respect to the internal wall of the cartridge 101.

In order to obtain a complete full-prepacked mixing system, a monomer liquid container 32, for example in the form of an ampoule made of glass or plastics that can be fractured, can be arranged in the container 134, which can be arranged on the rear side of the conveying plunger 103 for this purpose. The monomer liquid container 32 can contain the monomer liquid 6. The internal space of the container 134 can be connected in fluid-permeable manner to the second hollow space 107 via the fluid opening 108. By this means, a monomer liquid 6 released in the container 134 can flow from the container 134 into the second hollow space 107, when the device is held or set up with the cartridge head downwards.

A ring sleeve 136 with an internal thread can be attached to a rear-side end of the cartridge 101 that is opposite from the cartridge head. This simplifies the assembly of the device provided it is present as a part that is separate from cartridge 101. For this purpose, the ring sleeve 136 can be screwed into an internal thread on the rear-side end of the cartridge 101 by means of a matching external thread.

According to a preferred development, the present embodiment can provide the container 134 to include an external thread on its external circumference. Particularly in one embodiment, said external thread matches the internal thread of the ring sleeve 136 or an internal thread on the rear-side end of the cartridge 101. By this means, the container 134 can be screwed into the cartridge 101. This can enable a propulsion of the conveying plunger 103 in the internal space of the cartridge 101. Theoretically, as an alternative to the container 134, a cylinder (not illustrated) with a matching external thread can be attached to or loosely arranged on the rear side of the conveying plunger 103 such that the conveying plunger 103 and, by means of the conveying plunger 103, the dispensing plunger 104 as well can be pushed inside the internal space of the cartridge 101 in the direction of the cartridge head by the cylinder being screwed in.

One embodiment can provide a pore filter 140 to be arranged in or on the dispensing plunger 104. The feedthroughs 109 can be covered by the pore filter 140. This prevents cement powder 5 from the first hollow space from penetrating into the feedthroughs 109 or into the second hollow space 107, where it would form a gel like barrier upon reaction with the monomer liquid 6 and thus counteract the distribution of the monomer liquid 6 in the cement powder 5.

The pore filter 140 can in one embodiment be a circular disk. The pore filter 140 can be covered by a disk 142 and can be attached in the dispensing plunger 104. To enable and/or facilitate the monomer liquid 6 being conducted through and distributed in the first hollow space and in the cement powder 5, a multitude of boreholes or holes can be provided in the disk 142.

Multiple pins 148 can be arranged in the internal space of the container 134. Said pins 148 can touch against a cartridge base 58 of the monomer liquid container 32. The pins 148 can be used to fracture the monomer liquid container 32 at the cartridge base 58 or to puncture or cut the monomer liquid container 32 such as to open it. In one embodiment, the pins 148 can be arranged around the merging site of the fluid opening 108. The pins 148 can be situated at an appropriate distance from each other such that they do not cover an extension of the fluid opening 108 in order to enable the closure means 110 to pass through.

In contrast to the first exemplary embodiment according to FIGS. 1 to 10, the closure means 110 be connected to the dispensing plunger 104 in non-rigid manner in the second exemplary embodiment according to FIG. 11, but rather the closure means 110 can be screwed into an internal thread 166 on the rear side of the dispensing plunger 104 by means of an external thread 164. By this means, a variable level of the closure means 110 can be set such that the minimum distance between the conveying plunger 103 and the dispensing plunger 104 from which the fluid opening 108 is closed by the closure means 110 can be set.

The features of embodiments disclosed in the preceding description and in the claims, figures, and exemplary embodiments, can be essential for the implementation of the various embodiments both alone and in any combination.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A device for the production of a bone cement dough from a monomer liquid and a cement powder as starting components of the bone cement dough, and for dispensing of the bone cement dough, the device comprising
   a cartridge with a cylindrical internal space;
   a cartridge head with a dispensing opening for dispensing the bone cement dough, whereby the cartridge head closes the cartridge on a front side of the cartridge except for the dispensing opening;
   a conveying plunger that is arranged in the internal space of the cartridge and is supported in the internal space of the cartridge such that it is pushable in the direction of the dispensing opening;
   a dispensing plunger that is arranged in the internal space of the cartridge between the dispensing opening and the conveying plunger and that is supported in the internal space of the cartridge such that it is pushable in the direction of the dispensing opening;
   a first hollow space that is bordered by the cartridge head, by internal walls of the cartridge, and by the dispensing plunger, whereby the cement powder is arranged in the first hollow space;
   a second hollow space that is part of the cylindrical internal space of the cartridge, whereby the second hollow space is bordered by the dispensing plunger and the conveying plunger;
   a fluid opening that is arranged in the conveying plunger and through which the monomer liquid is conveyable into the second hollow space;
   a feedthrough that is arranged in the dispensing plunger and/or in the wall of the cartridge and which connects the first hollow space and the second hollow space in monomer liquid-permeable, but cement powder impermeable manner, and
   a closure means that is arranged on a rear side of the dispensing plunger that faces away from the dispensing opening, whereby the closure means projects away from the dispensing plunger in the direction of the conveying plunger and is situated at a distance from the fluid opening in the conveying plunger, whereby the fluid opening is closable with the closure means when the conveying plunger is being pushed in the direction of the dispensing opening, and whereby the closure means is appropriately mobile in the fluid opening closed by the closure means such that the fluid opening stays closed, while the conveying plunger is pushable further in the direction of the dispensing plunger.

2. The device according to claim 1, wherein a front side of the conveying plunger that faces the dispensing plunger and the rear side of the dispensing plunger are shaped with matching surfaces with respect to each other such that the front side of the conveying plunger touches against the rear side of the dispensing plunger such that the surfaces match when the conveying plunger is pushed against the dispensing plunger, whereby preferably the volume of the second hollow space thereby is reducible to a maximum of 1% of the volume of the second hollow space in a starting state, whereby the at least one closure means is situated at a distance from the at least one fluid opening in the starting state.

3. The device according to claim 1, wherein a front side of the conveying plunger that faces the dispensing plunger comprises a surface that tapers continuously in the direction of the fluid opening, and the rear side of the dispensing plunger comprises a surface that matches it like a negative shape and tapers continuously in the direction of the closure means.

4. The device according to claim 1, wherein a front side of the conveying plunger that faces the dispensing plunger comprises a depression with a funnel-shaped surface whose lowest point has the fluid opening arranged in it, and in that the rear side of the dispensing plunger comprises a projecting, cone-shaped surface of the same slope as the funnel-shaped surface, whereby the closure means is arranged on the tip of the cone-shaped surface.

5. The device according to claim 4, wherein the funnel-shaped surface on the front side of the conveying plunger comprises an angle of slope of at least 60°, and the cone-shaped surface on the rear side of the dispensing plunger comprises a matching angle of slope of at least 60°.

6. The device according to claim 1, wherein the closure means is a cylindrical rod that projects away from the rear side of the dispensing plunger by a length of at least 10 mm.

7. The device according to claim 1, wherein a container is arranged on a rear side of the conveying plunger that faces away from the dispensing plunger, with a monomer liquid container containing the monomer liquid being arranged in the container, which is an ampoule made of glass or plastics, whereby the monomer liquid container is openable inside the container and whereby the container is connected to the second hollow space in fluid-permeable manner via the fluid opening, whereby an opening means is arranged on a side of the container opposite from the conveying plunger, by means of which the monomer liquid container is openable inside the container, whereby the opening means is a sleeve attached to a cap, whereby the cap is screwable onto a thread of the container and the cap comprises a counter-thread for this purpose such that, when the cap is being screwed on, the monomer liquid container is pushed, by the sleeve, onto at least one projecting pin on the internal side of the container and thus the monomer liquid container is breakable open.

8. The device according to claim 7, wherein the container comprises an external thread that is screwable into an internal thread on an end of the cartridge opposite from the cartridge head, whereby the conveying plunger is pushable in the direction of the dispensing opening by screwing the container into the cartridge and the dispensing plunger is pushable by the conveying plunger in the direction of the dispensing opening, whereby the internal thread preferably is part of a ring sleeve that is connected to the cartridge on the end of the cartridge opposite from the cartridge head.

9. The device according to claim 1, wherein the length of the closure means is appropriate such that the volume of the second hollow space is at most equal to the volume of the monomer liquid conducted through the fluid opening, in particular of the monomer liquid contained in the monomer liquid container, when the tip of the closure means encounters and closes the fluid opening.

10. The device according to claim 1, wherein the closure means is cylindrical in shape and the fluid opening has a matching shape, whereby the closure means has a cylindrical shape with a circular footprint and the fluid opening is a circular or cylindrical hole.

11. The device according to claim 1, wherein the dispensing opening has a stopper arranged in it that closes the dispensing opening impermeable to the cement powder, which closes the dispensing opening permeable to gases, whereby the stopper is arranged in the dispensing opening such as to be mobile such that the stopper is pushable out of the dispensing opening by pressing on the ready-mixed bone cement dough, whereby it has a marker means that is visible from outside attached to the stopper, whose position is readable from outside to indicate whether the stopper is pushed outward in the dispensing opening.

12. The device according to claim 1, wherein a detachably attached foot is arranged on the cartridge head, whereby the foot is at least partially transparent, whereby a part of the foot facing the cartridge head is non-transparent and a part of the foot facing away from the cartridge head is transparent.

13. A method for the production of a pasty polymethylmethacrylate bone cement dough, whereby the bone cement dough is produced from a cement powder and a monomer liquid with a device according to claim 1, characterized by the following steps proceeding in the order given:
  A) conducting the monomer liquid through the fluid opening into the second hollow space;
  B) pushing the conveying plunger in the direction of the dispensing plunger until the closure means on the rear side of the dispensing plunger closes the fluid opening;
  C) pushing the conveying plunger further in the direction of the dispensing plunger, whereby the monomer liquid is pushed from the second hollow space into the cement powder in the first hollow space, with the closure means being pushed through the fluid opening or more deeply into the fluid opening and the fluid opening remaining closed;
  D) the conveying plunger pushing the dispensing plunger in the direction of the dispensing opening, whereby the bone cement dough produced in the first hollow space flows out through the dispensing opening.

14. The method according to claim 13, wherein the device is set up or held with the cartridge head (2) downwards in step A), and preferably in steps B) and C) as well, and gas inclusions escape from the second hollow space through the fluid opening.

15. The method according to claim 13, wherein the conveying plunger touches against the dispensing plunger in step D) with matching surfaces and the volume of the second hollow space is reduced, in step C), completely to zero or down to a maximum of 1% of the volume of the second hollow space in a starting state.

16. The method according to claim 13, wherein the pressure acting on the bone cement dough in step D) moves or pushes forward a stopper in the dispensing opening, whereby the stopper is removed from the dispensing opening subsequently and, if applicable, a foot is removed from the cartridge head and then an application tube is attached to the cartridge head of the cartridge.

17. The method according to claim 13, wherein a monomer liquid container containing the monomer liquid is opened in a container before step A) and the monomer liquid is released in the container, whereby the container is arranged on a rear side of the conveying plunger that faces away from the dispensing plunger, and the monomer liquid flows from the container through the fluid opening into the second hollow space in step A), whereby the conveying plunger in steps B) and C) and the conveying plunge and the dispensing plunger in step D) are driven by the container being pushed or screwed into the cartridge.

* * * * *